(12) United States Patent
Takahashi et al.

(10) Patent No.: US 9,725,514 B2
(45) Date of Patent: Aug. 8, 2017

(54) CHRONIC REJECTION INHIBITOR

(75) Inventors: Masafumi Takahashi, Nagano (JP); Atsushi Izawa, Nagano (JP)

(73) Assignees: Shinshu University, Nagano (JP); Chugai Seiyaku Kabushiki Kaisha, Tokyo (JP)

( * ) Notice: Subject to any disclaimer, the term of this patent is extended or adjusted under 35 U.S.C. 154(b) by 1 day.

(21) Appl. No.: 12/524,041

(22) PCT Filed: Jan. 23, 2008

(86) PCT No.: PCT/JP2008/050842
§ 371 (c)(1),
(2), (4) Date: Sep. 18, 2009

(87) PCT Pub. No.: WO2008/090901
PCT Pub. Date: Jul. 31, 2008

(65) Prior Publication Data
US 2010/0061986 A1  Mar. 11, 2010

(30) Foreign Application Priority Data
Jan. 23, 2007 (JP) ................................. 2007-012572

(51) Int. Cl.
*A61K 39/395* (2006.01)
*C07K 16/28* (2006.01)
*A61K 39/00* (2006.01)

(52) U.S. Cl.
CPC .... *C07K 16/2866* (2013.01); *A61K 2039/505* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,216,128 A | 6/1993 | Novick et al. |
| 5,530,101 A | 6/1996 | Queen et al. |
| 5,621,077 A | 4/1997 | Novick et al. |
| 5,639,455 A | 6/1997 | Shimamura et al. |
| 5,670,373 A | 9/1997 | Kishimoto |
| 5,795,965 A | 8/1998 | Tsuchiya et al. |
| 5,817,790 A | 10/1998 | Tsuchiya et al. |
| 5,856,135 A | 1/1999 | Tsuchiya et al. |
| 5,888,510 A | 3/1999 | Kishimoto et al. |
| 6,074,643 A | 6/2000 | Barbera-Guillem |
| 6,121,423 A | 9/2000 | Tsuchiya et al. |
| 6,261,560 B1 | 7/2001 | Tsujinaka et al. |
| 6,552,083 B1 | 4/2003 | Isobe et al. |
| 6,723,319 B1 | 4/2004 | Ito et al. |
| 7,291,721 B2 | 11/2007 | Giles-Komar et al. |
| 7,320,792 B2 | 1/2008 | Ito et al. |
| 7,414,024 B2 | 8/2008 | Blay et al. |
| 7,479,543 B2 | 1/2009 | Tsuchiya et al. |
| 7,521,052 B2 | 4/2009 | Okuda et al. |
| 7,781,617 B2 | 8/2010 | Kudou et al. |
| 7,824,674 B2 | 11/2010 | Ito et al. |
| 8,226,611 B2 | 7/2012 | Chen et al. |
| 8,470,316 B2 | 6/2013 | Yasunami |
| 8,623,355 B2 | 1/2014 | Okada et al. |
| 8,771,686 B2 | 7/2014 | Ishida |
| 9,017,677 B2 | 4/2015 | Mihara |
| 2001/0001663 A1 | 5/2001 | Kishimoto et al. |
| 2002/0119150 A1 | 8/2002 | Kirk et al. |
| 2004/0018540 A1 | 1/2004 | Yamamura et al. |
| 2004/0170626 A1 | 9/2004 | Schuurman et al. |
| 2005/0096257 A1 | 5/2005 | Shima et al. |
| 2005/0142635 A1 | 6/2005 | Tsuchiya et al. |
| 2005/0158317 A1 | 7/2005 | Blay et al. |
| 2005/0182007 A1 | 8/2005 | McSwiggen et al. |

(Continued)

FOREIGN PATENT DOCUMENTS

| | | |
|---|---|---|
| CN | 1164194 A | 11/1995 |
| CN | 1297357 A | 5/2001 |

(Continued)

OTHER PUBLICATIONS

Idezawa, T., et al., "Interleukin-6 Functions as an Autocrine Invasion Factor of Human Pancreatic Cancer Cells," *Yamanashi Med. J.* 19(2):53-67, University of Yamanashi, Japan (2004).

Extended European Search Report in European Patent Appl. No. 08 703 686.9, Applicants Shinshu University, et al., mailed on Aug. 24, 2010, European Patent Office, The Netherlands.

International Preliminary Report on Patentability with Written Opinion of the International Searching Authority for International Application No. PCT/JP2008/050842, mailed on Jul. 28, 2009, The International Bureau of WIPO, Switzerland.

Alvarez, B., et al., "Tumor necrosis factor-$\alpha$ exerts interleukin-6-dependent and -independent effects on cultured skeletal muscle cells," *Biochim. et Biophysica Acta* 1542:66-72, Elsevier Science B.V., Netherlands (2002).

(Continued)

*Primary Examiner* — Michael Pak
(74) *Attorney, Agent, or Firm* — Sterne, Kessler, Goldstein & Fox P.L.L.C.

(57) ABSTRACT

The present inventors assessed the effect of anti-IL-6 receptor antibodies in suppressing chronic rejection reaction. They assessed the effect of anti-mouse IL-6 receptor antibody (MR16-1) administration in suppressing the chronic rejection reaction using a mouse model for post-heart-transplantation chronic rejection. The result of histopathological analysis of transplanted hearts extirpated 60 days after transplantation revealed that fibrosis of myocardium and vascular stenotic lesions, which are pathological conditions characteristic of the chronic rejection reaction, were significantly suppressed in the MR16-1-treated group as compared to the control group. Thus, MR16-1 administration was demonstrated to have the effect of suppressing chronic rejection reaction. Specifically, the present inventors discovered for the first time that the rejection reaction in the chronic phase after organ transplantation was suppressed by administering an anti-IL-6 receptor antibody.

8 Claims, 2 Drawing Sheets

(56) References Cited

U.S. PATENT DOCUMENTS

| | | |
|---|---|---|
| 2006/0039902 A1 | 2/2006 | Young et al. |
| 2006/0111316 A1 | 5/2006 | Lawless |
| 2006/0165696 A1 | 7/2006 | Okano et al. |
| 2006/0188502 A1 | 8/2006 | Giles-Komar et al. |
| 2006/0193772 A1 | 8/2006 | Ochiai et al. |
| 2006/0251653 A1 | 11/2006 | Okuda et al. |
| 2006/0292147 A1 | 12/2006 | Yoshizaki et al. |
| 2007/0036785 A1 | 2/2007 | Kishimoto et al. |
| 2007/0134242 A1 | 6/2007 | Nishimoto et al. |
| 2007/0167425 A1 | 7/2007 | Nakade et al. |
| 2008/0081041 A1 | 4/2008 | Nemeth |
| 2009/0022719 A1* | 1/2009 | Mihara et al. ............ 424/133.1 |
| 2009/0022726 A1 | 1/2009 | Zaki et al. |
| 2009/0028784 A1 | 1/2009 | Garcia-Martinez et al. |
| 2009/0220499 A1 | 9/2009 | Yasunami |
| 2009/0220500 A1 | 9/2009 | Kobara |
| 2009/0263384 A1 | 10/2009 | Okada et al. |
| 2009/0269335 A1 | 10/2009 | Nakashima et al. |
| 2010/0008907 A1 | 1/2010 | Nishimoto et al. |
| 2010/0034811 A1 | 2/2010 | Ishida |
| 2010/0061986 A1 | 3/2010 | Takahashi et al. |
| 2010/0129357 A1 | 5/2010 | Garcia-Martinez et al. |
| 2010/0298542 A1 | 11/2010 | Igawa et al. |
| 2011/0098450 A1 | 4/2011 | Igawa et al. |
| 2011/0111406 A1 | 5/2011 | Igawa et al. |
| 2011/0150869 A1 | 6/2011 | Mitsunaga et al. |
| 2011/0245473 A1 | 10/2011 | Igawa et al. |
| 2012/0045453 A1 | 2/2012 | Chen et al. |
| 2012/0183539 A1 | 7/2012 | Maeda |
| 2013/0202588 A1 | 8/2013 | Nishimura |
| 2016/0139117 A1 | 5/2016 | Yamamura et al. |

FOREIGN PATENT DOCUMENTS

| | | |
|---|---|---|
| CN | 1694894 A | 11/2005 |
| CN | 1849135 A | 10/2006 |
| EP | 0 628 639 A1 | 12/1994 |
| EP | 0 721 783 A1 | 7/1996 |
| EP | 0 783 893 A1 | 7/1997 |
| EP | 0 791 359 A1 | 8/1997 |
| EP | 0 811 384 A1 | 12/1997 |
| EP | 0 931 544 A2 | 7/1999 |
| EP | 0 983 767 A1 | 3/2000 |
| EP | 1 074 268 A1 | 2/2001 |
| EP | 1 108 435 A1 | 6/2001 |
| EP | 1 197 210 A1 | 4/2002 |
| EP | 1 374 900 A1 | 1/2004 |
| EP | 1 562 968 | 5/2004 |
| EP | 1 690 550 A1 | 8/2006 |
| EP | 1 707 215 A1 | 10/2006 |
| EP | 1 941 907 A1 | 7/2008 |
| EP | 1 967 207 A1 | 9/2008 |
| EP | 1 967 209 A1 | 9/2008 |
| EP | 1 990 060 A1 | 11/2008 |
| EP | 2 025 346 A1 | 2/2009 |
| EP | 2 305 306 A1 | 6/2009 |
| EP | 2 578 233 A1 | 4/2013 |
| ES | 2 276 525 T3 | 6/2007 |
| FR | 2 694 767 A1 | 2/1994 |
| IE | 0 791 359 A1 | 8/1997 |
| JP | 6-237772 A | 8/1994 |
| JP | 07-046998 A | 2/1995 |
| JP | H07-505609 | 6/1995 |
| JP | 8 208514 A | 8/1996 |
| JP | 08-208514 A | 8/1996 |
| JP | 11-180873 A | 7/1999 |
| JP | 2002-527354 A | 8/2002 |
| JP | 2004-028926 A | 1/2004 |
| JP | 2005-524606 A | 8/2005 |
| JP | 2005-281235 A | 10/2005 |
| JP | 2006-524685 A | 11/2006 |
| JP | 2007-528691 A | 10/2007 |
| JP | 2008-37875 A | 2/2008 |
| JP | 2008-37876 A | 2/2008 |
| JP | 2008-538931 A | 11/2008 |
| JP | 2008-297315 A | 12/2008 |
| JP | 2010-527615 A | 8/2010 |
| RU | 2 127 117 C1 | 3/1999 |
| RU | 2 147 442 C1 | 4/2000 |
| RU | 2430111 C1 | 9/2009 |
| TW | 2008/03895 A | 1/2008 |
| TW | 201021829 A1 | 6/2010 |
| WO | WO 92/19759 A1 | 11/1992 |
| WO | WO 93/08817 A1 | 5/1993 |
| WO | WO 94/20488 A1 | 9/1994 |
| WO | WO 94/28159 A1 | 12/1994 |
| WO | WO 95/09873 A1 | 4/1995 |
| WO | WO 96/11020 A1 | 4/1996 |
| WO | WO 96/12503 A1 | 5/1996 |
| WO | WO 96/25174 A1 | 8/1996 |
| WO | WO 98/36061 A2 | 8/1998 |
| WO | WO 98/42377 A1 | 10/1998 |
| WO | WO 99/47170 A1 | 9/1999 |
| WO | WO 99/60013 A2 | 11/1999 |
| WO | WO 00/10607 A1 | 3/2000 |
| WO | WO 01/05394 A1 | 1/2001 |
| WO | WO 01/45678 A2 | 6/2001 |
| WO | WO 02/03492 A1 | 1/2002 |
| WO | WO 02/080969 A1 | 10/2002 |
| WO | WO 03/048205 A2 | 6/2003 |
| WO | WO 03/105861 A1 | 12/2003 |
| WO | WO 2004/007701 A1 | 1/2004 |
| WO | WO 2004/039826 A1 | 5/2004 |
| WO | WO 2004/045507 A2 | 6/2004 |
| WO | WO 2004/045512 A2 | 6/2004 |
| WO | WO 2004/071404 A2 | 8/2004 |
| WO | WO 2004/073741 A1 | 9/2004 |
| WO | WO 2004/096273 A1 | 11/2004 |
| WO | WO 2005/028514 A1 | 3/2005 |
| WO | WO 2005/037315 A1 | 4/2005 |
| WO | WO 2005/044848 A1 | 5/2005 |
| WO | WO 2005/061000 A1 | 7/2005 |
| WO | WO 2005/107800 A1 | 11/2005 |
| WO | WO 2006/009092 A1 | 1/2006 |
| WO | WO 2006/070286 A2 | 7/2006 |
| WO | WO 2006/072954 A2 | 7/2006 |
| WO | WO 2006/119115 A2 | 11/2006 |
| WO | WO 2007/043641 A1 | 4/2007 |
| WO | WO 2007/046489 A1 | 4/2007 |
| WO | WO 2007/058194 A1 | 5/2007 |
| WO | WO 2007/061029 A1 | 5/2007 |
| WO | WO 2007/067976 A2 | 6/2007 |
| WO | WO 2007/076927 A1 | 7/2007 |
| WO | WO 2007/086490 A1 | 8/2007 |
| WO | WO 2007/116962 | 10/2007 |
| WO | WO 2007/143168 A2 | 12/2007 |
| WO | WO 2008/020079 A1 | 2/2008 |
| WO | WO 2008/090901 A1 | 7/2008 |
| WO | WO 2008/144763 A2 | 11/2008 |
| WO | WO 2009/010539 A2 | 1/2009 |
| WO | WO 2009/041613 A1 | 4/2009 |
| WO | WO 2009/041621 A1 | 4/2009 |
| WO | WO 2009/125825 A1 | 10/2009 |
| WO | WO 2009/148148 A1 | 12/2009 |
| WO | WO 2010/107108 A1 | 9/2010 |
| WO | WO 2011/013786 A1 | 2/2011 |
| WO | WO 2011/149051 A1 | 12/2011 |
| WO | WO 2012/118750 A2 | 9/2012 |
| WO | WO 2014/200018 A1 | 12/2014 |

OTHER PUBLICATIONS

Barton-Davis, E.R., et al., "Viral mediated expression of insulin-like growth factor I blocks the aging-related loss of skeletal muscle function," *Proc. Natl. Acad. Sci. USA* 95:15603-15607, The National Academy of Sciences, United States (1998).

Bogdanovich, S., et al., "Functional improvement of dystrophic muscle by myostatin blockade," *Nature* 420:418-421, Nature Publishing Group, England (2002).

Bork, P., "Powers and Pitfalls in Sequence Analysis: The 70% Hurdle," *Genome Research* 10:398-400, Cold Spring Harbor Laboratory Press, United States (2000).

Brenner, S.E., "Errors in genome annotation," *Trends in Genetics* 15:132-133, Elsevier Science, United States (1999).

(56) References Cited

OTHER PUBLICATIONS

Dangott, B., et al., "Dietary creatine monohydrate supplementation increases satellite cell mitotic activity during compensatory hypertrophy," *Int. J. Sports Med.* 21:13-16, Georg Thieme Verlag, Germany (2000).
Darr, K.C. and Schultz, E., "Hindlimb suspension suppresses muscle growth and satellite cell proliferation," *J. Appl. Physiol.* 67:1827-1834, American Physiological Society, United States (1989).
Doerks, T., "Protein annotation: detective work for function prediction," *Trends in Genetics* 14:248-250, Elsevier Science Ltd., United States (1998).
Fisniku, O., et al., "Protective effects of PG490-88 on chronic allograft rejection by changing intragraft gene expression profiles," *Transplantation Proceedings* 37:1962-1964, Elsevier Inc., United States (2005).
Fredj, S., et al., "Role of interleukin-6 in cardiomyocyte/cardiac fibroblast interactions during myocyte hypertrophy and fibroblast proliferation," *J. Cell. Physiol.* 204:428-436, Wiley-Liss, Inc., United States (2005).
Garry, D.J., et al., "Persistent expression of MNF identifies myogenic stem cells in postnatal muscles," *Developmental Biology* 188:280-294, Academic Press, United States (1997).
Garry, D.J., et al., "Myogenic stem cell function is impaired in mice lacking the *forkhead*/winged helix protein MNF," *Proc. Natl. Acad. Sci. USA* 97:5416-5421, National Academy of Sciences, United States (2000).
Guice, K.S., et al., "Anti-tumor necrosis factor antibody augments edema formation in caerulein-induced acute pancreatitis," *Journal of Surgical Research* 51:495-499, Academic Press, Inc., United States (1991).
Hocking, D.C., et al., "Mechanisms of pulmonary edema induced by tumor necrosis factor-α," *Circulation Research* 67:68-77, American Heart Association, United States (1990).
Jejurikar, S.S., et al., "Skeletal muscle denervation increases satellite cell susceptibility to apoptosis," *Plast. Reconstr. Surg.* 110:160-168, Lippincott Williams & Wilkins, United States (2002).
Kami, K., et al., "Gene expression of receptors for IL-6, LIF, and CNTF in regenerating skeletal muscles," *J. Histochem. Cytochem.* 48:1203-1213, The Histochemical Society, Inc., United States (2000).
Knulst, A.C., et al., "Cytokine detection and modulation in acute graft vs. host disease in mice," *Mediators of Inflammation* 3:33-40, Hindawi Publishing Corporation, United States (1994).
Kobara, M., et al., "Antibody against interleukin-6 receptor attenuates left ventricular remodelling after myocardial infarction in mice," *Cardiovascular Research* 87:424-430, European Society of Cardiology, France (2010).
Kurek, J.B., et al., "Up-regulation of leukaemia inhibitory factor and interleukin-6 in transected sciatic nerve and muscle following denervation," *Neuromusc. Disord.* 6:105-114, Elsevier Science Ltd., Great Britain (1996).
Kurek, J.B., et al., "The role of leukemia inhibitory factor in skeletal muscle regeneration," *Muscle & Nerve* 20:815-822, John Wiley & Sons, Inc., United States (1997).
Matsuda, T., et al., "Establishment of an interleukin 6 (IL 6)/B cell stimulatory factor 2-dependent cell line and preparation of anti-IL 6 monoclonal antibodies," *Eur. J. Immunol.* 18:951-956, VCH Verlagsgesellschaft mbH, Germany (1988).
Matsushita, K., et al., "Interleukin-6/soluble interleukin-6 receptor complex reduces infarct size via inhibiting myocardial apoptosis," *Laboratory Investigation* 85:1210-1223, U.S. and Canadian Academy of Pathology, Inc., United States (2005).
Mauro, A., "Satellite cell of skeletal muscle fibers," *J. Biophys. Biochem. Cytol.* 9:493-495, Rockefeller Institute for Medical Research, United States (1961).
McCormick, K.M. and Schultz, E., "Role of satellite cells in altering myosin expression during avian skeletal muscle hypertrophy," *Developmental Dynamics* 199:52-63, Wiley-Liss, Inc., United States (1994).

Moss, F.P. and Leblond, C.P., "Satellite cells as the source of nuclei in muscles of growing rats," *Anat. Rec.* 170:421-436, A.R. Liss, United States (1971).
Mozdziak, P.E., et al., "Quantitation of satellite cell proliferation in vivo using image analysis," *Biotechnic & Histochemistry* 69:249-252, Williams & Wilkins, England (1994).
Mozdziak, P.E., et al., "Hindlimb suspension reduces muscle regeneration," *Eur. J. Appl. Physiol.* 78:136-140, Springer-Verlag, Germany (1998).
Mozdziak, P.E., et al., "Unloading of juvenile muscle results in a reduced muscle size 9 wk after reloading," *J. Appl. Physiol.* 88:158-164, American Physiological Society, United States (2000).
Mozdziak, P.E., et al., "Muscle regeneration during hindlimb unloading results in a reduction in muscle size after reloading," *J. Appl. Physiol.* 91:183-190, American Physiological Society, United States (2001).
Mukaida, N., et al., "Cytokines and immune network," *Rinsho Kensa* 35:447-452, Japan (1991).
Murata et al., "Development mechanism and pathophysiology," *The Saishin-Igaku* 47:49-56, Japan (1992).
Murphy, R., et al., "The effect of mechanical stretch on proliferation and differentiation of C2C12 cells," *Experimental Biology 2004: Meeting Abstracts:* A743, Abstract No. 476.6, American Association of Immunologists, United States (2004).
Ngo, J.T., et al., *Computational Complexity, Protein Structure Prediction, and the Levinthal Paradox,* in The Protein Folding Problem and Tertiary Structure Prediction 433-440 and 492-495 (Merz, K. and Le Grand, S. ed., 1994).
Phillips, A.J., "The challenge of gene therapy and DNA delivery," *J. Pharmacy and Pharmacology* 53:1169-1174, John Wiley & Sons, Inc., United Kingdom (2001).
Pirollo, K.F. and Chang, E.H., "Targeted Delivery of Small Interfering RNA: Approaching Effective Cancer Therapies," *Cancer Res.* 68:1247-1250, American Association for Cancer Research, United States (2008).
Quentmeier, H., et al., "Role of IL-6, IL-2, and IL-4 in the in vitro induction of cytotoxic T cells," *J. Immunology* 149:3316-3320, The American Association of Immunologists, United States (1992).
Schultz, E., et al., "Response of satellite cells to focal skeletal muscle injury," *Muscle & Nerve* 8:217-222, John Wiley & Sons, Inc., United States (1985).
Schultz, E., et al., "Acute effects of hindlimb unweighting on satellite cells of growing skeletal muscle," *J. Appl. Physiol.* 76:266-270, American Physiological Society, United States (1994).
Schultz, E., "Satellite cell proliferative compartments in growing skeletal muscles," *Developmental Biology* 175:84-94, Academic Press, Inc., United States (1996).
Shimizu, H., et al., "KRP-203, a novel synthetic immunosuppressant, prolongs graft survival and attenuates chronic rejection in rat skin and heart allografts," *Circulation* 111:222-229, American Heart Association, Inc., United States (2005).
Shimizu, K. and Oku, N., "Cancer anti-angiogenic therapy," *Biol. Pharm. Bull.* 27:599-605, Pharmaceutical Society of Japan, Japan (2004).
Skolnick, J. and Fetrow, J.S., "From genes to protein structure and function: novel applications of computational approaches in the genomic era," *Trends in Biotechnology* 18:34-39, Elsevier Science Ltd., United States (2000).
Snow, M.H., "Myogenic cell formation in regenerating rat skeletal muscle injured by mincing. II. An autoradiographic study." *Anat. Rec.* 188:201-217, A.R. Liss, United States (1977).
Snow, M.H., "Satellite cell response in rat soleus muscle undergoing hypertrophy due to surgical ablation of synergists," *Anat. Rec.* 227:437-446, Wiley-Liss, Inc., United States (1990).
Stan A.C., et al., "In vivo inhibition of angiogenesis and growth of the human U-87 malignant glial tumor by treatment with an antibody against basic fibroblast growth factor," *J. Neurosurg.* 82:1044-1052, American Association of Neurosurgeons, United States (1995).
Tamura, T., et al., "Soluble interleukin-6 receptors triggers osteoclast formation by interleukin 6," *Proc. Natl. Acad. Sci. USA* 90:11924-11928, Cell Biology (1993).

(56) References Cited

OTHER PUBLICATIONS

Tobe, T., et al., "Targeted disruption of the FGF2 gene does not prevent choroidal neovascularization in a murine model," *Am. J. Pathol.* 153:1641-1646, American Society for Investigative Pathology, United States (1998).

Tsujinaka, T., et al., "Interleukin 6 receptor antibody inhibits muscle atrophy and modulates proteolytic systems in interleukin 6 transgenic mice," *J. Clin. Invest.* 97:244-249, The American Society for Clinical Investigation, United States (1996).

Ulich, T.R., et al., "Intratracheal injection of endotoxin and cytokines," *Am. J. Pathol.* 138:1097-1101, American Association of Pathologists, United States (1991).

Unverified English language translation of Mukaida, N., et al., "Cytokines and immune network," *Rinsho Kensa* 35:447-452, Japan (1991).

Unverified English language translation of Murata et al., "Development mechanism and pathophysiology," *The Saishin-Igaku* 47:49-56, Japan (1992).

Vidal, L., et al., "Making sense of antisense," *European J. Cancer* 41:2812-2818, Elsevier Ltd., United States (2005).

Wang, X.D., et al., "Mechanical load-dependent regulation of satellite cell and fiber size in rat soleus muscle," *Am. J. Physiol. Cell. Physiol.* 290:C981-C989, American Physiological Society, United States (2006).

Warren, G.L., et al., "Physiological role of tumor necrosis factor α in traumatic muscle injury," *FASEB J.* 16:1630-1632, The Federation of American Societies for Experimental Biology, United States (2002).

Wells, J.A., "Additivity of Mutational Effects in Proteins," *Biochemistry* 29:8509-8517, American Chemical Society, United States (1990).

Restriction Requirement in U.S. Appl. No. 12/090,676, Kobara, M., et al., filed Oct. 20, 2006, mailed Mar. 12, 2010, U.S. Patent and Trademark Office, Alexandria, VA.

Restriction Requirement in U.S. Appl. No. 12/085,065, Okada, M., et al., filed Nov. 15, 2006, mailed Apr. 30, 2010, U.S. Patent and Trademark Office, Alexandria, VA.

Restriction Requirement in U.S. Appl. No. 12/090,061, Yasunami, Y., et al., filed Oct. 13, 2006, mailed Aug. 27, 2010, U.S. Patent and Trademark Office, Alexandria, VA.

Restriction Requirement in U.S. Appl. No. 12/296,193, Nishimoto, N., et al., filed Apr. 6, 2007, mailed Oct. 5, 2010, U.S. Patent and Trademark Office, Alexandria, VA.

Office Action in U.S. Appl. No. 12/090,676, Kobara, M., et al., filed Oct. 20, 2006, mailed Oct. 6, 2010, U.S. Patent and Trademark Office, Alexandria, VA.

Patel, N.S.A., et al., "Endogenous Interleukin-6 Enhances the Renal Injury, Dysfunction, and Inflammation Caused by Ischemia/Reperfusion," *J. Pharmacol. Exp. Ther.* 312(3):1170-1178, American Society for Pharmacology and Experimental Therapeutics, United States (2005).

Unverified English language tanslation of: Skurkovich, S.V., et al., "Anticytokine therapy—new approach to the treatment of autoimmune and cytokine-disturbance diseases," *Oncology and Immunopathology* 2:71-80 (2003) (relevant parts).

Skurkovich, S.V., et al., "Anticytokine therapy—new approach to the treatment of autoimmune and cytokine-disturbance diseases," *Oncology and Immunopathology* 2:71-80 (2003) (Russian).

Idezawa, T., et al., "Interleukin-6 Functions as an Autocrine Invasion Factor of Human Pancreatic Cancer Cells," *Yamanashi Med. J.* 20(2):xxxvi, University of Yamanashi, Japan (2005).

Unverified English language translation of: Idezawa, T., et al., "Interleukin-6 Functions as an Autocrine Invasion Factor of Human Pancreatic Cancer Cells," *Yamanashi Med. J.* 20(2):xxxvi, University of Yamanashi, Japan (2005).

Kamohara, H., et al., "IL-6 no Suigan Saibo no Zoshoku-Ten'i Oyobosu Eikyo to Kanshitsu Saibo ni yoru Hatsugen Seigyo Kiko," *Japanese Journal of Gastroenterological Surgery* 39(7):1356 (Abstract 2529), Japanese Journal of Gastroenterological Surgery, Japan (2006).

Unverified English language translation of: Kamohara, H., et al., "IL-6 no Suigan Saibo no Zoshoku-Ten'i Oyobosu Eikyo to Kanshitsu Saibo ni yoru Hatsugen Seigyo Kiko," *Japanese Journal Gastroenterological Surgery* 39(7):1356 (Abstract 2529), Japanese Journal of Gastroenterological Surgery, Japan (2006).

Amendment in Reply to Office Action of May 3, 2011, submitted Nov. 1, 2011, in U.S. Appl. No. 12/090,061, Yasunami, Y., et al., filed Oct. 13, 2006.

Bellomo, R., "The Cytokine Network in the Critically Ill," *Anaesth. Intensive Care* 20(3):288-302, Australian Society of Anaesthetists, Australia (Aug. 1992).

Benda, B. and Korsgren, O., "Interleukin-6 in Islet Xenograft Rejection," *Transplant Int.* 14:63-71, Springer-Verlag, Germany (2001).

Biswas, P.S., et al., "Involvement of IL-6 in the Paracrine Production of VEGF in Ocular HSV-1 Infection," *Exp. Eye Res.* 82:46-54, Elsevier Ltd., England (2006).

Borsellino, N., et al., "Blocking Signalling Through the Gp130 Receptor Chain by Interleukin-6 and Oncostatin M Inhibits PC-3 Cell Growth and Sensitizes the Tumor Cells to Etoposide and Cisplatin-Mediated Cytotoxicity," *Cancer* 85:134-144, American Cancer Society, USA (1999).

Campbell, I.L., et al., "Essential Role for Interferon-γ and Interleukin-6 in Autoimmune Insuline-Dependent Diabetes in NOD/Wehi Mice," *J. Clin. Invest.* 87:739-742, The American Society for Clinical Investigation, Inc., USA (Feb. 1991).

Campbell, I.L., et al., "Evidence for IL-6 Production by and Effects on the Pancreatic β-Cell," *J. Immunol.* 143(4):1188-1191, The American Society of Immunologists, USA (Aug. 1989).

Choi, S-E., et al., "IL-6 Protects Pancreatic Islet Beta Cells from Pro-Inflammatory Cytokines-Induced Cell Death and Functional Impairment in vitro and in vivo," *Transpl. Immunol.* 13:43-53, Elsevier B.V., The Netherlands (2004).

Culig, Z., et al., "Interleukin-6 Regulates Androgen Receptor Activity and Prostate Cancer Cell Growth," *Mol. Cell. Endocrinol.* 197:231-238, Elsevier Science Ireland Ltd., Ireland (2002).

Davies, G., et al., "The HGF/SF Antagonist NK4 Reverses Fibroblast- and HGF-Induced Prostate Tumor Growth and angiogenesis In Vivo," *Int. J. Cancer* 106:348-354, Wiley Liss, Inc., USA (2003).

Ding, W., et al., "The Change of Plasma Interleukin-6 Level and Cardiac Protective Effect of Monoclonal Antibody to IL-6 During Myocardial Infarction Reperfusion," *Chin. J. Cardiol.* 27(1):29-32, Chinese Medical Association Publishing House (Feb. 1991) (with English Abstract).

Eder, I.E., et al., "Targeting the Androgen Receptor in Hormone-Refractory Prostate Cancer—New Concepts," *Future Oncol.* 1(1):93-101, Future Medicine Ltd, England (2005).

Finkel, M.S., et al., "Negative Inotropic Effects of Cytokines on the Heart Mediated by Nitric Oxide," *Science* 257-387-389, American Association for the Advancement of Science, USA (Jul. 1992).

Ford, H.R., et al., "Evidence that Production of Interleukin 6 Within the Rejecting Allograft Coincides with Cytotoxic T Lymphocyte Development," *Transplantation* 51(3):656-661, Williams & Wilkins, USA (Mar. 1991).

Fuchs, M., et al., "Role of Interleukin-6 for LV Remodeling and Survival After Experimental Myocardial Infarction," *FASEB J* 17(14):2118-2120, The Federation of American Societies for Experimental Biology, USA (Nov. 2003).

Giugliano, G., et al., "Verapamil Inhibits Interleukin-6 and Vascular Endothelial Growth Factor Production in Primary Cultures of Keloid Fibroblasts," *Br. Assoc. Plast. Surg.* 56:804-809, Elsevier Ltd, England (2003).

Grossniklaus, H.E. and Green, R., "Choroidal Neovascularization," *Am. J. Ophthalmol.* 137:496-503, Elsevier Inc., USA (2004).

Gwechenberger, M. et al., "Cardiac Myocytes Product Interleukin-6 in Culture and in Viable Border Zone of Reperfused Infarctions," *Circulation* 99(4):546-551, American Heart Assocation, Inc., USA (1999).

Hirota, H., et al., "Continuous Activation of gp130, a Signal-Transducing Receptor Component for Interleukin 6-Related Cytokines, Causes Myocardial Hypertrophy in Mice," *Proc. Natl. Acad. Sci.* 92:4862-4866, The National Academy of Sciences, USA (May 1995).

(56) References Cited

OTHER PUBLICATIONS

Hoffman, S., et al., "Inhibitory Effects of Verapamil Isomers on the Proliferation of Choroidal Endothelial Cells," *Graefe's Arch. Clin. Exp. Ophthalmol.* 244:376-381, Springer-Verlag, Germany (2006).
Horinaga, M., et al., "Clinical and Pathologic Significance of Activation of Signal Transducer and Activator of Transcription 3 in Prostate Cancer," *Urology* 66:671-675, Elsevier Inc., USA (2005).
Ito, et al., "Regulation of Damage to Islets Transplanted into the Liver by IL-6 Receptor Antibody," *J. Japan Surg. Soc. 107* (special extra issue 2):387(#PS-014-5), 2006 (English Translation) (Abstract Only).
Itoh, T., et al., "Anti-IL-6 Receptor Antibody Down-Regulates Pro-Inflammatory Cytokine Production of Gr-1 *CD11b* Cells and Prevents Early Loss of Islet Grafts in the Liver of Mice in Association with Engraftments," *Transplantation* 82(Supp.3):Abstract No. 2838, World Transplant Congress (2006)(Abstract Only).
Jeron, A., et al., "Systemic Immunosuppression Fails to Suppress Cardiac Cytokine Induction in Pressure Overload Hypertrophy in Rats,"*Immunobiol.* 205:51-60, Urban & Fischer Verlag, Germany (2002).
Kallen, K-J., et al., "New Developments in IL-6 Dependent Biology and Therapy: Where Do We Stand and What are the Options?," *Exp. Opin. Invest. Drugs* 8(9):1327-1349, Ashley Publications Ltd., England (1999).
Kobara, M., et al., "Inhibition of Interleukin-6 Signaling Attenuates Left Ventricular Remodeling After Myocardial Infarction in Mice," *Circulation Supplement II* 112(17):Abstract 851, The American Heart Association, USA (Oct. 2005) (Abstract Only).
Kurdi, M., et al., "Increased Expression of IL-6 and LIF in the Hypertrophied Left Ventricle of TGR(mRen2)27 and SHR Rats," *Mol. Cell. Biochem.* 269:95-101, Springer, The Netherlands (2005).
Kuroda, K., et al., "Prevention of Cancer Cachexia by a Novel Nuclear Factor κB Inhibitor in Prostate Cancer," *Clin. Cancer Res.* 11(15):5590-5594, American Association for Cancer Research, USA (Aug. 2005).
Lee, S.O., et al., "Interleukin-6 Protects LNCaP Cells from Apoptosis Induced by Androgen Deprivation Through the Stat3 Pathway," *The Prostate* 60:178-186, Wiley-Liss, Inc., USA (2004).
Luo, H., et al., "A Proteasome Inhibitor Effectively Prevents Mouse Heart Allograft Rejection," *Transplantation* 72(2):196-202, Lippincott Williams & Wilkins, Inc., USA (Jul. 2001).
Nagai, et al., "Suppression of Experimental Choroid Neovascularization by Inhibition of Interleukin-6 Receptor," *Inflammation and Regeneration* 26(4):367 (#90), The Japanese Society of Inflammation and Regeneration, Japan (Jul. 2006) (English Translation) (Abstract Only).
Nakashima, J., et al., "Serum Interleukin 6 as a Prognostic Factor in Patients with Prostate Cancer," *Clin. Cancer Res.* 6:2702-2706, American Association for Cancer Research, USA (Jul. 2000).
Negoro, S., et al., "Activation of JAK/STAT Pathway Transduces Cytoprotective Signal in Rat Acute Myocardial Infarction,"*Cardiovas, Res.* 47:797-805, Elsevier Science B.V., The Netherlands (2000).
Nishimoto, N. and Kishimoto, T., "Inhibition of IL-6 for the Treatment of Inflammatory Diseases," *Curr. Opin. Pharmacol.* 4:386-391, Elsevier Ltd., England (2004).
Okamoto, M., et al., "Interleukin-6 as a Paracrine and Autocrine Growth Factor in Human Prostatic Carcinoma Cells in Vitro," *Cancer Res.* 57:141-146, American Association for Cancer Research, USA (Jan. 1997).
Okamoto, A. et al., "Inhibition of Interleukin-6 Signaling Attenuates Left Ventricular Remodeling After Experimental Myocardial Infarction," *J. Heart Failure Supplement* 11:P-066, Heart Failure Society of America, USA (2005)(Abstract Only).
Okazaki, M. et al., "Characterization of Anti-Mouse Interleukin-6 Receptor Antibody," *Immunol. Lett.*84:231-240, Elsevier Science B.V., The Netherlands (2002).
Ono, K., et al., "Cytokine Gene Expression After Myocardial Infarction in Rat Hearts," *Circulation* 98:149-156, American Heart Association, USA (1998).
Park, H., et al., "Interleukin-6 Protects MIN6 β Cells from Cytokine-Induced Apoptosis," *Ann. N.Y. Acad, Sci.* 1005:242-249, New York Academy of Sciences, USA(2003).
Paul, W.E., "Transplatation and Graft Rejection," in *Fundamental Immunology*, Third Edition, pp. 1124-1125, Raven Press, Ltd., USA (1993).
Paula, B., "Reappraisal of the Concept of Hormone Therapy in Metastatic Prostate Cancer and Implications for Treatment," *Eur. Urol.* 47:729-735, Elsevier B.V., The Netherlands (2005).
Pauleikhoff, D., "Neovascular Age-Related Macular Degeneration," *Retina* 25:1065-1084, Lippincott Williams & Wilkins, USA (2005).
Seddon, J.M., et al., "Progression of Age-Related Macular Degeneration," *Arch. Ophthalmol.* 123:774-782, American Medical Association, USA (Jun. 2005).
Shimazaki, et al., "Human Myeloma Model and Antitumor Effect of Anti-Human IL-6 Receptor Antibody," *Rinsho Ketsueki.* 38(4):281-284, The Japanese Society of Hematology, Japan (Apr. 1997) (English Translation).
Smith, P.C, and Keller, E.T., "Anti-Interleukin-6 Monoclonal Antibody Induces Regression of Human Prostate Cancer Xenografts in Nude Mice," *The Prostate* 48:47-53, Wiley-Liss, Inc., USA (2001).
Smith, T.F. and Zhang, X., "The Challenges of Genome Sequence Annotation or 'The Devil is in the Details'," *Nat. Biotechnol.* 15:1222-1223, Nature Publishing Group, USA (1997).
Trikha, M., et al., "Targeted Anti-Interleukin-6 Monoclonal Antibody Therapy for Cancer: A Review of the Rationale and Clinical Evidence," *Clin. Cancer Res.* 9:4653-4665, American Association for Cancer Research, USA (Oct. 2003).
Xing, Y., et al., "The Effect of Interleukin-6 on the Proliferation of Prostate Cancer Cellsin Vitro and the Modulation of This Procedure," *J. Tongji Med. Univ.* 21(3):225-227, Springer-Verlag, Germany (2001).
Yamauchi-Takihara, K., et al., "Hypoxic Stress Induces Cardiac Myocyte-Derived Interleukin-6," *Circulation* 91:1520-1524, The American Heart Association, USA (1995).
Yue, P., et al. "Cytokine Expression Increases in Nonmyocytes from Rats with Postinfarction Heart Failure," *Am. J. Physiol.* 275:H250-H258, American Physiological Society, USA (1998).
Zaki, M.H., et al, "CNTO 328, A Monoclonal Antibody to IL-6, Inhibits Human Tumor-Induced Cachexia in Nude Mice," *Int. J. Cancer* 111:592-595, Wiley-Liss, Inc., USA (2004).
Response to Restriction Requirement filed on Oct. 22, 2010, in U.S. Appl. No. 12/085,065, inventors Okada, M., et al., filed Nov. 15, 2006, U.S. Patent and Trademark Office, Alexander, VA.
Office Action mailed Nov. 26, 2010, in U.S. Appl. No. 12/085,065, inventors Okada, M., et al., filed Nov. 15, 2006, U.S. Patent and Trademark Office, Alexandria, VA.
Amendment and Reply to Office Action filed on May 25, 2011, in U.S. Appl. No. 12/085,065, inventors Okada, M., filed Nov. 15, 2006, U.S. Patent and Trademark Office, Alexandria, VA.
Response to Restriction Requirement filed Feb. 24, 2011 in U.S. Appl. No. 12/090,061, inventor Yasunami, Y., filed Oct. 13, 2006, U.S. Patent and Trademark Office, Alexandria.
Office Action mailed May 3, 2011, in U.S. Appl. No. 12/090,061, inventor Yasunami, Y., filed Oct. 13, 2006, U.S. Patent and Trademark Office, Alexandria.
Amendment and Reply to Office Action filed on Apr. 5, 2011, in U.S. Appl. No. 12/090,676, inventors Kobara, M., et al., filed Oct. 20, 2006, U.S. Patent and Trademark Office, Alexandria, VA.
Office Action mailed Jun. 8, 2011, in U.S. Appl. No. 12/090,676, inventors Kobara, M., et al., filed Oct. 20, 2006, U.S. Patent and Trademark Office, Alexandria, VA.
Office Action mailed Feb. 2, 2011, in U.S. Appl. No. 12/094,644, inventors Nakashima, J., et al., filed Nov. 24, 2006, U.S. Patent and Trademark Office, Alexandria, VA.
Response to Restriction Requirement filed Jul. 25, 2011, in U.S. Appl. No. 12/094,644, inventors Nakashima, J., et al., filed Nov. 24, 2006, U.S. Patent and Trademark Office, Alexandria, VA.
Office Action mailed Jan. 13, 2011, in U.S. Appl. No. 12/161,733, inventor Ishida, S., filed Jan. 26, 2007, U.S. Patent and Trademark Office, Alexandria, VA.

(56) References Cited

OTHER PUBLICATIONS

Response to Restriction Requirement filed Jul. 7, 2011, in U.S. Appl. No. 12/161,733, inventor Ishida, S., filed Jan. 26, 2007, U.S. Patent and Trademark Office, Alexandria, VA.
Response to Restriction Requirement filed on Nov. 2, 2010, in U.S. Appl. No. 12/296,193, inventors Nishimoto, N., et al., filed Apr. 6, 2007, U.S. Patent and Trademark Office, Alexandria, VA.
Office Action mailed Dec. 20, 2010, in U.S. Appl. No. 12/296,193, inventors Nishimoto, N., et al., filed Apr. 6, 2007, U.S. Patent and Trademark Office, Alexandria, VA.
Amendment and Reply to Office Action filed on Jun. 20, 2011, in U.S. Appl. No. 12/296,193, inventors Nishimoto, N., et al., filed Apr. 6, 2007, U.S. Patent and Trademark Office, Alexandria, VA.
Office Action mailed Jul. 26, 2011, in U.S. Appl. No. 12/296,193, inventors Nishimoto, N., et al., filed Apr. 6, 2007, U.S. Patent and Trademark Office, Alexandria, VA.
Extended European Search Report in European Patent Appl. No. 06 811 729.0, Applicants Fukuoka University, et al., mailed on Dec. 23, 2009, European Patent Office, The Netherlands (Not a Corresponding Application).
Extended European Search Report in European Patent Appl. No. 06 832 657.8, Applicants National Hospital Organization, et al., mailed on Dec. 3, 2009, European Patent Office, The Netherlands (Not a Corresponding Application).
Extended European Search Report in European Patent Appl. No. 06 812 073.2, Applicant Chugai Seiyaku Kabushiki Kaisha, mailed on Dec. 7, 2009, European Patent Office, The Netherlands (Not a Corresponding Application).
Extended European Search Report in European Patent Appl. No. 06 833 196.6, Applicant Keio University, et al., mailed on Sep. 8, 2009, European Patent Office, The Netherlands (Not a Corresponding Application).
Extended European Search Report in European Patent Appl. No. 07 707 458.1, Applicant Keio University, et al., mailed on Dec. 11, 2009, European Patent Office, The Netherlands (Not a Corresponding Application).
Extended European Search Report in European Patent Appl. No. 07 741 181.7, Applicant Osaka Univeristy, et al., mailed on Dec. 23,2009, European Patent Office, The Netherlands (Not a Corresponding Application).
International Search Report for International Application No. PCT/JP2008/320441, mailed on Dec. 19, 2006, Japanese Patent Office, Japan (Not a Corresponding Application).
International Preliminary Report on Patentability with Written Opinion of the International Searching Authority for International Application No. PCT/JP2006/320441, mailed on Apr. 16, 2008, The International Bureau of WIPO, Switzerland (Not a Corresponding Application).
International Search Report for International Application No. PCT/JP2006/322726, mailed on Jan. 9, 2007, Japanese Patent Office, Japan (Not a Corresponding Application).
International Preliminary Report on Patentability with Written Opinion of the International Searching Authority for International Application No. PCT/JP2006/322726, mailed on May 20, 2008. The International Bureau of WIPO, Switzerland (Not a Corresponding Application).
International Search Report for International Application No. PCT/JP2006/320905, mailed on Jan. 16, 2007, Japanese Patent Office, Japan (Not a Corresponding Application).
International Preliminary Report on Patentability with Written Opinion of the International Searching Authority for International Application No. PCT/JP2006/320905, mailed on Apr. 22, 2008, The International Bureau of WIPO, Switzerland (Not a Corresponding Application).
International Search Report for International Application No. PCT/JP2006/323392, mailed on Jan. 9, 2007, Japanese Patent Office, Japan (Not a Corresponding Application).
International Preliminary Report on Patentability with Written Opinion of the International Searching Authority for International Application No. PCT/JP2006/323392, mailed on May 27, 2008, The International Bureau of WIPO, Switzerland (Not a Corresponding Application).
International Search Report for International Application No. PCT/JP2007/051226, mailed on May 1, 2007, Japanese Patent Office, Japan (Not a Corresponding Application).
International Preliminary Report on Patentability with Written Opinion of the International Searching Authority for International Application No. PCT/JP2007/051226, mailed on Jul. 29, 2008, The International Bureau of WIPO, Switzerland (Not a Corresponding Application).
International Search Report for International Application No. PCT/JP2007/057745, mailed on Jul. 10, 2007, Japanese Patent Office, Japan (Not a Corresponding Application).
International Preliminary Report on Patentability with Written Opinion of the International Searching Authority for International Application No. PCT/JP2007/057745, mailed on Nov. 17, 2008, The International Bureau of WIPO, Switzerland (Not a Corresponding Application).
International Search Report for International Application No. PCT/JP2009/060314, mailed on Aug. 11, 2007, Japanese Patent Office, Japan (Not a Corresponding Application).
International Preliminary Report on Patentability with Written Opinion of the International Searching Authority for International Application No. PCT/JP2009/060314, mailed on Jan. 11, 2011, The International Bureau of WIPO, Switzerland (Not a Corresponding Application).
English language Abstract of Russian Patent Publication No. RU 2 127 117 C1, published Mar. 10, 1993, European Patent Office, Espacenet, Worldwide Database.
Akira, S. et al., "Interleukin-6 in Biology and Medicine," *Advances in Immunology* 54:1-78, Academic Press, Inc., San Diego, CA, USA (1993).
Unverified English language translation of French Patent No. FR 2 694 767 A1 (12 pages).
Furukawa, Y. et al., "Cytokine Gene Expression During the Development of Graft Coronary Artery Disease in Mice," *Japanese Circulation Journal* 63:775-782, Japanese Circulation Society, Kyoto, Japan (1999).
Hirano, T. et al., "Complementary DNA for a novel human interleukin (BSF-2) that induces B lymphocytes to produce immunoglobulin," *Nature* 324:73-76, Nature Publishing, London, UK (1986).
Hirata, Y. et al., "Characterization of IL-6 Receptor Expression by Monoclonal and Polyclonal Antibodies," *The Journal of Immunology* 143:2900-2906, The American Association of Immunologists (1989).
Hornick, P. et al., "Chronic Rejection in the Heart," *Methods in Molecular Biology* 333:131-144, Humana Press Inc., Torowa, NJ, USA (2006).
Huang, Y.-W. et al., "A Monoclonal Anti-Human IL-6 Receptor Antibody Inhibits the Proliferation of Human Myeloma Cells," *Hybridoma* 12:621-630, Mary Ann Liebert, Inc., Larchmont, NY, USA (1993).
International Search Report for International Application No. PCT/JP2008/050842, Japanese Patent Office, Japan, mailed on Feb. 19, 2008 (2 pages).
Izawa, A. et al., "Critical Role of Interleukin-6 and its Crosstalk with AT1R Signaling in Acute Rejection of Murine Cardiac Allografts," *Circulation Journal* 71 (*Suppl.* 1):392 (#PE-269), Annual Scientific Meeting of the Japanese Circulation Society, Kobe, Japan (2007).
Izawa, A. et al., "Interleukin-6 Blockade Attenuates the Development of Both Acute and Chronic Rejection of Murine Cardiac Allografts: A Potential Crosstalk between Interleukin-6 and Signaling through Angiotensin II Type 1 Receptor," *American Journal of Transplantation* 7(*Suppl* 11):426(#1084), American Transplant Congress, San Francisco, CA, USA (2007).
Lotz, M. et al., "B cell Stimulating Factor 2/Interleukin 6 is a Costimulant for Human Thymocytes and T Lymphocytes," *The Journal of Experimental Medicine* 167:1253-1258, Rockefeller University Press, New York, NY, USA (1988).

(56) References Cited

OTHER PUBLICATIONS

Novick, D. et al., "Monoclonal Antibodies to the Soluble Human IL-6 Receptor: Affinity Purification, ELISA, and Inhibition of Ligand Binding," *Hybridoma* 10:137-146, Mary Ann Liebert, Inc., Larchmont, NY, USA (1991).

Ramzy, D. et al., "Cardiac allograft vasculopathy : a review," *Canadian Journal of Surgery* 48:319-327, Canadian Medical Association, Ottawa, ON, Canada (2005).

Taga, T. et al., "Receptors for B Cell Stimulatory Factor 2: Quantitation, Specificity, Distribution, and Regulation of Their Expression," *The Journal of Experimental Medicine* 166:967-981, Rockefeller University Press, New York, NY, USA (1987).

Taga, T. et al., "Interleukin-6 Triggers the Association of its Receptor with a Possible Signal Transducer, gp130," *Cell* 58:573-581, Cell Press, Cambridge, MA, USA (1989).

Valantine, H., "Cardiac Allograft Vasculopathy After Heart Transplantation: Risk Factors and Management," *The Journal of Heart and Lung Transplantation* 23:S187-S193, Elsevier Science, New York, NY, USA (2004).

Webber, S.A. et al., "Heart and lung transplantation in children," *Lancet* 368:53-69, Lancet, London, UK (2006).

Wong, B.W. et al., "Progress in heart transplantation," *Cardiovascular Pathology* 14:176-180, Elsevier Science, New York, NY, USA (2005).

Yamasaki, K. et al., "Cloning and Expression of the Human Interleukin-6 (BSF-2/IFNβ2) Receptor," *Science* 241:825-828, American Association for the Advancement of Science, Washington, DC (1988).

Campochiaro, P.A., "Retinal and Choroidal Neovascularization," *J. Cell. Physiol.* 184:301-310, Wiley-Liss, Inc. (2000).

Chuntharapai, A., and Kim, K.J., "Generation of Monoclonal Antibodies to Chemokine Receptors," *Meth. Enzymol.* 288:15-27, Academic Press (1997).

Fujita, J. et al., "Anti-Interleukin-6 Receptor Antibody Prevents Muscle Atrophy in Colon-26 Adenocarcinoma-Bearing Mice with Modulation of Lysosomal and ATP-Ubiquitin-Dependent Proteolytic Pathways," *Int. J. Cancer* 68:637-643, Wiley-Liss, Inc. (1996).

Greenberg, A.S., et al., "Interleukin 6 Reduces Lipoprotein Lipase Activity in Adipose Tissue of Mice in Vivo and in 3T3-L1 Adipocytes: A Possible Role for Interleukin 6 in Cancer Cachexia," *Canc. Res.* 52:4113-4116, American Association for Cancer Research (1992).

Nishimoto, N. et al., "Anti-interleukin 6 receptor antibody treatment in rheumatic disease," *Ann. Rheum. Dis.* 59(suppl I):i21-i27, BMJ Group (2000).

Ohtsuka, T. et al., "Relation of Circulating Interleukin-6 to Left Ventricular Remodeling in Patients with Reperfused Anterior Myocardial Infarction," *Clin. Cardiol.* 27:417-420, John Wiley & Sons, Inc. (2004).

Ono, M. et al., "The effect of IL-6 on the des-gamma-carboxy prothrombin synthesis in human hepatoma cells," *Gastroenterologia Japonica* 27:745-750, The Japanese Society of Gastroenterology (1992).

Puhakka, M. et al., "Interleukin-6 and Tumor Necrosis Factor Alpha in Relation to Myocardial Infarct Size and Collagen Formation," *J. Cardiac Failure* 9:325-332, Elsevier Inc. (2003).

Q&A *de wakaru himan to tounyoubyou* 3:982-984 (2004), with unverified English language translation.

Sato, K. et al., "Reshaping a Human Antibody to Inhibit the Interleukin 6-dependent Tumor Cell Growth," *Canc. Res.* 53:851-856, American Association for Cancer Research (1993).

Strassman, G. et al., "Evidence for the Involvement of Interleukin 6 in Experimental Cancer Cachexia," *J. Clin. Invest.* 89:1681-1684, The American Society for Clinical Investigation, Inc. (1992).

Office Action mailed Apr. 11, 2012, in U.S. Appl. No. 12/085,065, inventors: Okada, M., et al., filed Nov. 15, 2006, U.S. Patent and Trademark Office, Alexandria, VA.

Office Action mailed Jan. 12, 2012, in U.S. Appl. No. 12/090,061, inventor: Yasunami, Y., filed Oct. 13, 2006, U.S. Patent and Trademark Office, Alexandria, VA.

Amendment and Reply to Office Action submitted Jun. 11, 2012, in U.S. Appl. No. 12/090,061, inventor: Yasunami, Y., filed Oct. 13, 2006, U.S. Patent and Trademark Office, Alexandria, VA.

Response to Restriction Requirement filed Aug. 31, 2010, in U.S. Appl. No. 12/090,676, inventor: Kobara, M., filed Oct. 20, 2006, U.S. Patent and Trademark Office, Alexandria, VA.

Amendment and Reply to Office Action submitted Mar. 21, 2012, in U.S. Appl. No. 12/094,644, inventors: Nakashima, J., et al., filed Nov. 24, 2006, U.S. Patent and Trademark Office, Alexandria, VA.

Office Action mailed May 22, 2012, in U.S. Appl. No. 12/094,644, inventors: Nakashima, J. et al., filed Nov. 24, 2006, U.S. Patent and Trademark Office, Alexandria, VA.

Amendment and Reply to Office Action submitted Feb. 15, 2012, in U.S. Appl. No. 12/161,733, inventor: Ishida, S., filed Jan. 26, 2007, U.S. Patent and Trademark Office, Alexandria, VA.

Office Action mailed Apr. 9, 2012, in U.S. Appl. No. 12/161,733, inventor: Ishida, S., filed Jan. 26, 2007, U.S. Patent and Trademark Office, Alexandria, VA.

Amendment and Reply to Office Action submitted Jan. 26, 2012, in U.S. Appl. No. 12/296,193, inventors: Nishimoto, N., et al., filed Apr. 6, 2007, U.S. Patent and Trademark Office, Alexandria, VA.

Amendment and Reply to Office Action submitted Mar. 19, 2012, in U.S. Appl. No. 12/296,193, inventors: Nishimoto, N., et al., filed Apr. 6, 2007, U.S. Patent and Trademark Office, Alexandria, VA.

Office Action mailed Jun. 1, 2012, in U.S. Appl. No. 12/996,162, inventors: Mitsunaga, S., et al., filed Jun. 5, 2009, U.S. Patent and Trademark Office, Alexandria, VA.

International Preliminary Report on Patentability for International Patent Application No. PCT/JP2010/062874, The International Bureau of WIPO, Geneva, Switzerland, issued Feb. 7, 2012 (Not a Corresponding Application).

Amendment and Reply to Office Action submitted Jun. 29, 2012, in U.S. Appl. No. 12/090,676, inventor: Kobara, M., filed Oct. 20, 2006, U.S. Patent and Trademark Office, Alexandria, VA.

English language Database Abstract for JP 6-237772 A, published Aug. 30, 1994, European Patent Office, Espacenet, Worldwide Database.

English language Abstract for JP 8-208514 A, published Aug. 13, 1996, European Patent Office, Espacenet, Worldwide Database.

Ashizawa, T., et al., "Clinical significance of interleukin-6 (IL-6) in the spread of gastric cancer: role of IL-6 as a prognostic factor," *Gastric Cancer* 8:124-131, International and Japanese Gastric Cancer Associations, Japan (2005).

Beck, J.T., et al., "Brief report: alleviation of systemic manifestations of Castleman's disease by monoclonal anti-interleukin-6 antibody," *N. Engl. J. Med.* 330:602-605, United States (1994).

Bond, M., et al., "Synergistic upregulation of metalloproteinase-9 by growth factors and inflammatory cytokines: an absolute requirement for transcription factor NF-κB," *FEBS Letters* 435:29-34, Federation of European Biochemical Societies (1998).

Campo, S., et al., "Comparative Activity of Sant7 and anti-IL-6, IL-6R monoclonal antibodies in a murine model of B-cell lymphoma," *Cytokine* 31:368-374, Elsevier Ltd., Netherlands (2005).

Choy, E., "Inhibiting interleukin-6 in rheumatoid arthritis," *Curr. Rheumatol. Rep.* 10:413-417, Current Medicine Group LLC, United States (2008).

Ewert, S., et al., "Stability improvement of antibodies for extracellular and intracellular applications: CDR grafting to stable frameworks and structure-based framework engineering," *Methods* 34:184-199, Elsevier Inc., Netherlands (2004).

Gao, S. P., et al., "Mutations in the EGFR kinase domain mediate STAT3 activation via IL-6 production in human lung adenocarcinomas," *J. Clin. Invest.* 117(12)3846-3856, The American Society for Clinical Investigation, United States (2007).

Ghosh, S. and Karin, M., "Missing Pieces in the NF-κB Puzzle," *Cell* 109: S81-S96, Cell Press, United States (2002).

Greten, F. R., et al., "IKKβ Links Inflammation and Tumorigenesis in a Mouse Model of Colitis-Associated Cancer," *Cell* 118:285:296, Cell Press, United States (2004).

(56) References Cited

OTHER PUBLICATIONS

Guerne, P-A., et al., "Synovium as a source of interleukin 6 in vitro. Contribution to local and systemic manifestations of arthritis," *J. Clin. Invest.*, 83:585-592, The American Society for Clinical Investigation, Inc., United States (1989).
Guillén, I., et al., "Cytokine signaling during myocardial infarction: sequential appearance of IL-1β and IL-6," *Am. J. Physiol.* 269(2 Pt2):R229-235, The American Physiological Society (1995).
Hanes, J., et al., "Picomolar affinity antibodies from a fully synthetic naive library selected and evolved by ribosome display," *Nat. Biotechnol.* 18:1287-1292, Nature America Inc. (2000).
Hirai, I., et al., "Perineural Invasion in Pancreatic Cancer," *Pancreas* 24(1):15-25, Lippincott Williams & Wilkins, Inc., United States (2002).
Hirano, T., et al., "Excessive production of interleukin 6/B cell stimulatory factor-2 in rheumatoid arthritis," *Eur. J. Immunol.* 18:1797-1801, VCH Verlagsgesellschaft mbH (1988).
Hirota, H., et al., "Loss of a gp130 Cardiac Muscle Cell Survival Pathway Is a Critical Event in the Onset of Heart Failure during Biomechanical Stress," *Cell* 97:189-198, Cell Press, United States (1999).
Houssiau, F.A., et al., "Interleukin-6 in synovial fluid and serum of patients with rheumatoid arthritis and other inflammatory arthritides," *Arthritis Rheum.* 31(6):784-788, John Wiley & Sons (1988).
Karin, M. and Lin, A., "NF-κB at the crossroads of life and death," *Nature Immunology* 3(3):221-227, Nature Publishing Group, England (2002).
Karin, M., et al., "NF-κB in Cancer: From Innocent Bystander to Major Culprit," *Nature Reviews Cancer* 2:301-310, Nature Publishing Group, England (2002).
Kishimoto, T., "The biology of interleukin-6," *Blood* 74(1):1-10, The American Society of Hematology, United States (1989).
Kotake, S., et al., "Interleukin-6 and soluble interleukin-6 receptors in the synovial fluids from rheumatoid arthritis patients are responsible for osteoclast-like cell formation," *J. Bone Miner Res.* 11(1):88-95, Blackwell Science, Inc. (1996).
Madhok, R., et al., "Serum interleukin 6 levels in rheumatoid arthritis: correlations with clinical and laboratory indices of disease activity," *Ann. Rheum. Dis.* 52:232-234, BMJ Group, United Kingdom (1993).
Maeda, S., et al., "IKKβ Couples Hepatocyte Death to Cytokine-Driven Compensatory Proliferation that Promotes Chemical Hepatocarcinogenesis," *Cell* 121:977-990, Elsevier Inc., Netherlands (2005).
Maeda, S., et al., "Ikappa B Kinase β/Nuclear Factor-κB Activation Controls the Development of Liver Metastasis by Way of Interleukin-6 Expression," *Hepatology* 50(6):1851-1860, The American Association for the Study of Liver Diseases (2009).
Martignoni, M.E., et al., "Role of Mononuclear Cells and Inflammatory Cytokines in Pancreatic Cancer-Related Cachexia," *Clin. Cancer Res.* 11(16):5802-5808, American Association for Cancer Research (2005).
Matzaraki, V., et al., "Evaluation of serum procalcitonin and interleukin-6 levels as markers of liver metastasis," *Clinical Biochemistry* 40:336-342, Elsevier Inc., United States (2007).
Miyamoto, Y., et al., "Interleukin-6 Inhibits Radiation Induced Apoptosis in Pancreatic Cancer Cells," *Anticancer Research* 21:2449-2456 (2001).
Naugler, W. E., et al., "Gender Disparity in Liver Cancer Due to Sex Differences in MyD88-Dependnet IL-6 Production," *Science* 317:121-124, American Association for the Advancement of Science, United States (2007).
Nishimoto, N., et al., "Interleukin 6: from bench to bedside," *Nat. Clin. Pract. Rheumatol.* 2(11):619-626, Nature Publishing Group, England (2006).
Okada, Y., et al., "Experimental Implication of Celiac Ganglionotropic Invasion of Pancreatic-Cancer Cells Bearing *c-ret* Proto-Oncogene With Reference to Glial-Cell-Line-Derived Neurotrophic Factor (GDNF)," *Int. J. Cancer* 81:67-73, Wiley-Liss, Inc. (1999).

Pikarsky, E., et al., "NF-κB functions as a tumour promoter in inflammation-associated cancer," *Nature* 431:461-466, Nature Publishing Group, England (2004).
Sack, U., et al., "Interleukin-6 in synovial fluid is closely associated with chronic synovitis in rheumatoid arthritis," *Rheumatol. Int.* 13:45-51, Springer-Verlag (1993).
Sansone, P., et al., "IL-6 triggers malignant features in mammospheres from human ductal breast carcinoma and normal mammary gland," *J. Clin. Invest.* 117(12):3988-4002, The American Society for Clinical Investigation, United States (2007).
Sarkar, F. H., et al., "Back to the Future: COX-2 Inhibitors for Chemoprevention and Cancer Therapy," *Mini-Reviews in Medicinal Chemistry* 7:599-608, Bentham Science Publishers Ltd., Netherlands (2007).
Steeg, P.S., "Tumor metastasis: mechanistic insights and clinical challenges," *Nature Medicine* 12(8):895-904, Nature Publishing Group, England (2006).
Steeg, P. S. and Theodorescu, D., "Metastasis: a therapeutic target for cancer," *Nature Clinical Practice Oncology* 5(4):206-219, Nature Publishing Group, England (2008).
Studebaker, A. W., et al., "Fibroblasts Isolated from Common Sites of Breast Cancer Metastasis Enhance Cancer Cell Growth Rates and Invasiveness in an Interleukin-6-Dependent Manner," *Cancer Res* 68(21):9087-9095, American Association for Cancer Research, United States (2008).
Takahashi, H., et al., "Antiproteases in Preventing the Invasive Potential of Pancreatic Cancer Cells," *J. Pancreas* 8(4 Suppl.):501-508 (2007).
Takeda, K., et al., "Murine Tumor Cells Metastasizing Selectively in the Liver: Ability to Produce Hepatocyte-activating Cytokines Interleukin-1 and/or-6," *Jpn. J. Cancer Res.* 82:1299-1308, John Wiley & Sons, Inc., United States (1991).
Tisdale, M.J., "Biology of cachexia," *J. Natl. Cancer Inst.* 89(23):1763-1773, Oxford University Press, England (1997).
Wilansky, S., "Echocardiography in the Assessment of Complications of Myocardial Infarction," *Tex. Heart Inst. J.* 18(4):237-242, Texas Heart Institute (1991).
Yamakawa, Y., et al., "Astrocytes Promote the Proliferation of Lung Cancer Cells in Brain Metastases via inflammatory cytokines, especially IL-6" *Neuroscience* 48:216, P-22 (poster presentation) (2009).
Amendment and Reply to Office Action submitted Oct. 9, 2012, in U.S. Appl. No. 12/085,065, inventors Okada, M., et al., filed Nov. 15, 2006, U.S. Patent and Trademark Office, Alexandria, VA.
Office Action mailed Jan. 11, 2013, in U.S. Appl. No. 12/085,065, inventors Okada, M., et al., filed Nov. 15, 2006, U.S. Patent and Trademark Office, Alexandria, VA.
Amendment and Reply to Office Action submitted Jun. 11, 2012, in U.S. Appl. No. 12/090,061, inventor Yasunami, Y., filed Oct. 13, 2006, U.S. Patent and Trademark Office, Alexandria, VA.
Office Action mailed May 22, 2012, in U.S. Appl. No. 12/094,644, inventors Nakashima, J., et al., filed Nov. 24, 2006, U.S. Patent and Trademark Office, Alexandria, VA.
Office Action mailed Jun. 1, 2012, in U.S. Appl. No. 12/996,162, inventors Mitsunaga, S., et al., filed Jun. 5, 2009, U.S. Patent and Trademark Office, Alexandria, VA.
Amendment and Reply to Office Action submitted Jun. 28, 2012, in U.S. Appl. No. 12/996,162, inventors Mitsunaga, S., et al., filed Jun. 5, 2009, U.S. Patent and Trademark Office, Alexandria, VA.
Office Action mailed Sep. 12, 2012, in U.S. Appl. No. 12/996,162, inventors Mitsunaga, S., et al., filed Jun. 5, 2009, U.S. Patent and Trademark Office, Alexandria, VA.
Co-pending U.S. Appl. No. 13/700,355, inventors Nishimura, T., et al., filed Nov. 27, 2012 (Not Yet Published).
International Search Report for International Application No. PCT/JP2010/062874, mailed Aug. 31, 2010, Japanese Patent Office, Japan (Not a Corresponding Application).
Ceyhan, G.O. et al., "Neural invasion in pancreatic cancer: A mutual tropism between neurons and cancer cells," *Biochem. Biophys. Res. Comm.* 374:442-447, Elsevier Inc. (2008).

(56) References Cited

OTHER PUBLICATIONS

Maeda, S. et al., "Essential Roles of Ikkβ / Nf-κB Activation for Development of Liver Metastasis in Mice," *Gastroenterol.* 130:P-1-P-350, Supplement 2, AASLD Abstracts, p. A-750, abstract No. 107, Elsevier Inc. (2006).

Maeda, S. et al., "Role of IKKβ / NF-κB Activation for Development of Liver Metastatis," Supplement: The 58th Annual Meeting of the American Association for the Study of Liver Diseases, *Hepatol. 46:Issue Supplement S1*, AASLD Abstracts, p. 518A, abstract No. 630, American Association for the Study of Liver Diseases (2007).

Huang, C., et al., "Inhibitory effect of AG490 on invasion and metastasis of human pancreatic cancer cells in vitro," *Chin. J. Oncol.* 28:890-893, Wanfang Data Co., Ltd., Beijing, China (2006).

Huang, C., et al., "Inhibition of STAT3 activity with AG490 decreases the invasion of human pancreatic cancer cell in vitro," *Cancer Science* 97:1417-1423, Japanese Cancer Association, Tokyo, Japan (2006).

Nishimoto, N., "Clinical Studies in Patients With Castleman's Disease, Crohn's Disease, and Rheumatoid Arthritis in Japan," *Clinical Reviews in Allergy & Immunology* 28:221-229, Humana Press, United States (2005).

Okada, S., et al., "Elevated Serum Interleukin-6 Levels in Patients with Pancreatic Cancer," *Japanese Journal of Clinical Oncology* 28:12-15, Foundation of Clinical Oncology, Tokyo, Japan (1998).

Roitt, I., et al., "Immunology," Fifth Edition, *110,* Mir, Moscow, Russia (2000).

Unverified English translation of: Roitt, I., et al., "Immunology," Fifth Edition, *110,* Mir, Moscow, Russia (2000).

Yokota, S., et al., "Clinical Study of Tocilizumab in Children With Systemic-Onset Juvenile Idiopathic Arthritis," *Clinical Reviews in Allergy & Immunology* 28:231-237, Humana Press, United States (2005).

Restriction Requirement in U.S. Appl. No. 13/387,292, Maeda, S., filed Jul. 30, 2010, mailed Jan. 31, 2013, U.S. Patent and Trademark Office, Alexandria, VA.

Response to Restriction Requirement filed on Mar. 1, 2013, in U.S. Appl. No. 13/387,292, inventor Maeda, S., filed Jul. 30, 2010, U.S. Patent and Trademark Office, Alexandria, VA.

Amendment and Reply to Office Action submitted Mar. 12, 2013, in U.S. Appl. No. 12/996,162, inventors Mitsunaga, S., et al., filed Jun. 5, 2009, U.S. Patent and Trademark Office, Alexandria, VA.

Office Action mailed Mar. 20, 2013, in U.S. Appl. No. 12/996,162, inventors Mitsunaga, S., et al., filed Jun. 5, 2009, U.S. Patent and Trademark Office, Alexandria, VA.

Office Action mailed Mar. 26, 2013, in U.S. Appl. No. 13/387,292, inventors Maeda, S., et al., filed Jul. 30, 2010, U.S. Patent and Trademark Office, Alexandria, VA.

Notice of Allowance for U.S. Appl. No. 12/090,061, inventor Yasunami, Y., filed Oct. 13, 2006, U.S. Patent and Trademark Office, Alexandria, VA.

Yoshio-Hoshino, N. et al., "Establishment of a New Interleukin-6 (IL-6) Receptor Inhibitor Applicable to the Gene Therapy for IL-6-Dependent Tumor," *Cancer Res.* 67:871-875, American Association for Cancer Research (2007).

Ogata, T. et al., "Early administration of IL-6RA does not prevent radiation-induced lung injury in mice," *Radiation Oncology* 5:26, BioMed Central, London (2010).

Ogata, T. et al., "Anti-IL-6 receptor antibody does not ameliorate radiation pneumonia in mice," *Exp. Ther. Med.* 4:273-276, Spandidos Publications, Greece (2012).

Amendment and Reply filed Jul. 11, 2013, in U.S. Appl. No. 12/085,065, § 371(c) date of Jun. 1, 2009, inventors: Okada, M., et al., U.S. Patent and Trademark Office, Alexandria, VA.

Akira, S., et al., "The evidence for interleukin-6 as an autocrine growth factor in malignancy," *Cancer Biology* 3:17-26 (1992).

Armstrong, C.A., et al., "Melanoma-Derived Interleukin 6 Inhibits In Vivo Melanoma Growth," *Journal of Investigative Dermatology* 102:278-284 (1994).

Becker, Y., "Molecular Immunological Approaches to Biotherapy of Human Cancers—A Review, Hypothesis, and Implications," *Anticancer Research* 26:1113-1134 (2006).

Cabillic, F., et al., "Interleukin-6 and vascular endothelial growth factor release by renal cell carcinoma cells impedes lymphocyte-dendritic cell cross-talk," *Clinical and Experimental Immunology* 146:518-523 (2006).

Duluc, D., et al., "Tumor-associated leukemia inhibitory factor and IL-6 skew monocyte differentiation into tumor-associated macrophage-like cells," *Blood* 110 (13):4319-4330 (2007).

Porgador, A., et al., "Interleukin 6 Gene Transfection into Lewis Lung Carcinoma Tumor Cells Suppresses the Malignant Phenotype and Confers Immunotherapeutic Competence against Parental Metastatic Cells," *Cancer Research* 52:3679-3686 (1992).

Sebba, A., "Tocilizumab: The first interleukin-6-receptor inhibitor," *American Journal of Health-System Pharmacy* 65:1413-1418 (2008).

Suzuki, E., et al., "Gemcitabine Selectively Eliminates Splenic Gr-1[+]/CD11 b[+] Myeloid Suppressor Cells in Tumor-Bearing Animals and Enhances Antitumor Immune Activity," *Clinical Cancer Research* 11(18):6713-6721 (2005).

Tanaka, F., et al., "The Anti-Human Tumor Effect and Generation of Human Cytotoxic T Cells in SCID Mice Given Human Peripheral Blood Lymphocytes by the in Vivo Transfer of the Interleukin-6 Gene Using Adenovirus Vector," *Cancer Research* 57:1335-1343 (1997).

Vincent, J., et al., "5-Fluorouracil Selectively Kills Tumor-Associated Myeloid-Derived Suppressor Cells Resulting in Enhanced T Cell-Dependent Antitumor Immunity," *Cancer Research* 70(8):3052-3061(2010).

Zangari, M., et al., "Immunomodulatory drugs in multiple myeloma," *Expert Opinion on Investigative Drugs* 14(11):1411-1418 (2005).

Hanahan D. and Weinberg, R.A., "Hallmarks of Cancer: The Next Generation," *Cell* 144:646-674, Elsevier, Inc. (2011)

Tsuchiya, M., "Therapeutic Antibody," Credit Suisse Seminar at Fuji-Gotemba Research Laboratories, p. 21, Shizuoka, Japan (2006).

Unverified English translation of Tsuchiya, M., "Therapeutic Antibody," Credit Suisse Seminar at Fuji-Gotemba Research Laboratories, p. 21, Shizuoka, Japan (2006).

Hatzi, E., et al., "N-*myc* oncogene overexpression down-regulates IL-6; evidence that IL-6 inhibits angiogenesis and suppresses neuroblastoma tumor growth," *Oncogene* 21:3552-3561, Nature Publishing Group, England (2002).

Konopatskaya, O., et al., "VEGF$_{165}$b, an Endogenous C-Terminal Splice Variant of VEGF, Inhibits Retinal Neovascularisation in Mice," *Invest. Ophthalmol. Vis. Sci.* 47:E-Abstract 1749-B836, Association for Research in Vision and Ophthalmology, Inc. (2006).

Mitsunaga, S., et al., "Detail Histologic Analysis of Nerve Plexus Invasion in Invasive Ductal Carcinoma of the Pancreas and Its Prognostic Impact," *Am J Surg Pathol* 31:1636-1644, Lippincott Williams & Wilkins, United States (2007).

Mitsunaga, S., et al., "Nerve invasion distance is dependent on laminin γ2 in tumors of pancreatic cancer," *International Journal of Cancer* 127:805-819, UICC, United States (2010).

Kitazawa, R., et al., "Interleukin-1 Receptor Antagonist and Tumor Necrosis Factor Binding Protein Decrease Osteoclast Formation and Bone Resorption in Ovariectomized Mice," *J. Clin. Invest* 94:2397-2406, The American Society for Clinical Investigation, Inc., United States (1994).

Stan, A.C., et al., "In vivo inhibition of angiogenesis and growth of the human U-87 malignant glial tumor by treatment with an antibody against basic fibroblast growth factor," *J Neurosurg* 82(6):1044-1052, American Association of Neurological Surgeons, United States (1995).

Tobe, T., et al., "Targeted Disruption of the FGF2 Gene Does Not Prevent Choroidal Neovascularization in a Murine Model," *Am. J. of Pathology* 153(5):1641-1646, American Society of Investigative Pathology, United States (1998).

(56) References Cited

OTHER PUBLICATIONS

Lancaster, J.M., et al., "Identification of genes associated with ovarian cancer metastasis using microarray expression analysis," *Int J Gynecol Cancer* 16:1733-1745, International Gynecologic Cancer Society, United States (2006).
Sacchi, A., et al., "Treatment With Monoclonal Antibody to a Lewis Lung Carcinoma-Associated Antigen: Different Effects on Primary Tumor and Its Metastases," *Cancer Treatment Reports* 69 (9):985-991, Oxford University Press, United Kingdom (1985).
Chung, Y.-C. and Y.F. Chen, "Serum Interleukin-6 Levels Reflect the Disease Status of Colorectal Cancer," *J. Surgical Oncology* 83:222-226, Wiley-Liss, Inc., United States (2003).
Fujiwara, et al., "Control of tumor immunity by B cells and Th2 cytokines," *Annual Review Men'eki* 1999:257-269 (1999).
Kan, S., et al., "The effect of anti-cancer agents on CD4+FoxP3+ regulatory T cell," *Dai 68 Kai Annual Meeting of the Japan Cancer Association,* p. 286, P-0539 (2009).
Michalaki, Y., et al., "Serum levels of IL-6 and TNF-α correlate with clinicopathological features and patient survival in patients with prostate cancer," *British Journal of Cancer* 90:2312-2316, Cancer Research UK, United Kingdom (2004).
Narita, et al., "Gemcitabine selectively depletes $CD11b^+$ $Gr-1^+$ immature myeloid cells in tumor-bearing mice and enhances anti-tumor immune response," *Society for Fundamental Cancer Immunology Sokai Shoroku* 10:49 (2006).
Yamamoto, N., et al., "Regulatory Mechanisms for Production of IFN-γ and TNF by Antitumor T Cells or Macrophages in the Tumor-Bearing State," *Journal of Immunology* 154(5):2281-2290, The American Association of Immunologists, United States (1995).
Zhang, G.-J. and I. Adachi, "Serum Interleukin-6 Levels Correlate to Tumor Progression and Prognosis in Metastatic Breast Carcinoma," *Anticancer Research* 19:1427-1432, International Institute of Anticancer Research, Greece (1999).
International Search Report for International Patent Application No. PCT/JP2011/062209, Japanese Patent Office, Japan, mailed on Jul. 12, 2011.
Unverified English language translation of Fujiwara, et al., "Control of tumor immunity by B cells and Th2 cytokines," *Annual Review Men'eki* 1999:257-269 (1999).
Unverified English language translation of Narita, et al., "Gemcitabine selectively depletes $CD11b^+Gr-1^+$immature myeloid cells in tumor-bearing mice and enhances anti-tumor immune response," *Society for Fundamental Cancer Immunology Sokai Shoroku* 10:49 (2006).
Unverified English language translation of TW 201021839 A1, published Jun. 16, 2010, in the name of Chugai Seiyaku Kabushiki Kaisha.
Jones, S.W., et al., "Disuse atrophy and exercise rehabilitation in humans profoundly affects the expression of genes associated with the regulation of skeletal muscle mass," *FASEB J.* 18: 1025-1027, The Federation of American Societies for Experimental Biology (2004).
Berger, T. et al., "Disruption of the *Lcn2* gene in mice suppresses primary mammary tumor formation but does not decrease lung metastasis," *Proc. Natl. Acad. Sci.* 107(7):2995-3000 (2010).
Kim, S. et al., "Carcinoma-produced factors activate myeloid cells through TLR2 to stimulate metastasis," *Nature* 457:102-106 (2009).
Shewach, D.S. et al., "Gemcitabine and radiosensitization in human tumor cells," *Investigational New Drugs* 14:257-263 (1996).
Ito, N., et al., "Induction of Interleukin-6 by Interferon Alfa and Its Abrogation by a Serine Protease Inhibitor in Patients With Chronic Hepatitis C," *Hepatology* 23(4):669-675, American Association for the Study of Liver Diseases, United States (1996).
Tantraworasin, A., et al., "Prognostic factors of tumor recurrence in completely resected non-small cell lung cancer," *Cancer Management and Research* 5:77-84, Dove Medical Press, United Kingdom (2013).
Kayahara, M., et al., "The Nature of Neural Invasion by Pancreatic Cancer," *Pancreas* 35(3):218-223, Lippincott Williams & Wilkins, United States (2007).

Kitazawa, R., et al., "Interleukin-1 Receptor Antagonist and Tumor Necrosis Factor Binding Protein Decrease Osteoclast Formation and Bone Resorption in Ovariectomized Mice," *J. Clin. Invest.* 94:2397-2406, The American Society for Clinical Investigations, Inc., United States (1994).
Lancaster, J.M., et al., "Identification of genes associated with ovarian cancer metastasis using microarray expression analysis," *Int. J. Gynecol. Cancer* 16:1733-1745, Lippincott Williams & Wilkins, United States (2006).
Latulippe, E., et al., "Comprehensive Gene Expression Analysis of Prostate Cancer Reveals Distinct Transcriptional Programs Associated with Metastatic Disease," *Cancer Research* 62:4499-4506, American Association for Cancer Research, United States (2002).
MedlinePlus, U.S. National Library of Medicine NIH National Institutes of Health, "Liver metastases," http://www.nlm.nih.gov/medlineplus/ency/article/000277.htm, accessed Nov. 22, 2014.
National Cancer Institute, U.S. National Institutes of Health, "Metastatic Cancer: Questions and Answers," http://web.archive.org/web/20100110123630/http://www.cancer.gov/publications, accessed Nov. 22, 2014.
Poli, V., et al., "Interleukin-6 deficient mice are protected from bone loss caused by estrogen depletion," *The EMBO Journal* 13(5):1189-1196, Oxford University Press, United Kingdom (1994).
Sacchi, A., et al., "Treatment With Monoclonal Antibody to a Lewis Lung Carcinoma-Associated Antigen: Different Effects on Primary Tumor and Its Metastases," *Cancer Treatment Reports* 69(9):985-991, Oxford University Press (1985).
Sugahara, H., et al., "Expression of Interleukin-6 in Human Intrahepatic Biliary Tract and its Pathologic Significance; An Immunohistochemical and In situ Hybridization Study," *J. Juzen Med. Soc.* 105:819-833, Japan (1996).
Kayahara, M., et al., "Neural Invasion and Lymph Node Metastasis in the Head of the Pancreas Carcinoma," *The Japanese Journal of Gastroenterological Surgery* 24(3):813-817, The Japanese Society of Gastroenterological Surgery, Japan (1991).
Nakamura, T., "Cancer prevention by NK 4 to act as an inhibitor of tumor invasion, metastasis and angiogenesis," The Basics and Clinical Aspects of Angiogenesis—[II] Angiogenesis and Tumors, 8. Invasion/Metastasis/tumor Suppression of Angiogenesis-Inhibitory Factor AK 4, pp. 57-66, Japanese Association of Medical Sciences (2002).
Unverified English language translation of Nakamura, T., "Cancer prevention by NK 4 to act as an inhibitor of tumor invasion, metastasis and angiogenesis," The Basics and Clinical Aspects of Angiogenesis—[II] Angiogenesis and Tumors, 8. Invasion/Metastasis/tumor Suppression of Angiogenesis-Inhibitory Factor AK 4, pp. 57-66, Japanese Association of Medical Sciences (2002).
Yan, L., "(II) Abdominal discomfort and pain," *Theory and Practice of Oncology,* Shandong Science and Technology Press, 2 pages (2006).
Zijun, L., "Tissue Infiltration," *Tumor Metastasis,* Shanxi Science and Technology Press, 5 pages (2007).
Bertagnolli, M.M. et al. "IL-4-Supported Induction of Cytolytic T Lymphocytes Requires IL-2 and IL-6," *Cellular Immunology* 133:327-341, Academic Press, United States (1991).
Borg, A.J., et al., "15-Deoxyspergualin inhibits interleukin 6 production in in vitro stimulated human lymphocytes," *Transplant Immunology* 4:133-143, Elsevier, Netherlands (1996).
Bork, P. and Bairoch, A., "Go hunting in sequence databases but watch out for the traps," *Trends in Genetics* 12:425-427, Elsevier Science Ltd. United Kingdom (1996).
Charge, S.B.P. and Rudnicki, M.A., "Cellular and Molecular Regulation of Muscle Regeneration," *Physiology Reviews* 84:209-238, The American Physiological Society, United States (2004).
Fraunberger, P., et al., "Cytokine and Cytokine-Receptor Profiles After Liver and Heart Transplant," *Transplantation Proceedings* 27:2023-2027, Appleton & Lange, United States (1995).
Hudes, G.R., et al., "Preliminary results of a phase I study: A chimeric monoclonal anti IL-6 antibody CNTO 328 in combination with docetaxel in patients with hormone refractory prostate cancer," *Journal of Clinical Oncology* 25(18S): 15521, American Society of Clinical Oncology, United States (2007) (Abstract for ASCO Annual Meeting).

(56) References Cited

OTHER PUBLICATIONS

Kanda, T. and Takahashi, T., "Interleukin-6 and Cardiovascular Diseases," *Japanese Heart Journal* 45:183-193, Japanese Heart Journal Association, Japan (2004).

Kitahara, M. et al., "The in vivo Anti-tumor Effect of Human Recombinant Interleukin-6," *Japanese Journal of Cancer Research* 81:1032-1038, Elsevier Science Publishers, Netherlands (1990).

Ming, J.E., et al., "IL-6 enhances the generation of cytolytic T lymphocytes in the allogeneic mixed leucocyte reaction," *Clinical Experimental Immunology* 89:148-153, Blackwell Scientific Publications, Netherlands (1992).

Okada, M., et al., "IL-6/BSF-2 Functions as a Killer Helper Factor in the In Vitro Induction of Cytotoxic T Cells," *The Journal of Immunology* 141:1543-1549, The American Association of Immunologists, United States (1988).

Salgado, R., et al., "Circulating Interleukin-6 Predicts Survival in Patients With Metastatic Breast Cancer," *Int. J. Cancer* 103:642-646, Wiley-Liss, Inc., United States (2003).

Snow, M.H., "Myogenic Cell Formation in Regenerating Rat Skeletal Muscle Injured by Mincing: I. A Fine Structural Study," *Anat. Rec.* 188:181-200, The Wistar Institute of Anatomy and Biology, United States (1977).

Weyand, M., et al., "Serial Interleukin-6 Blood Levels Early After Cardiac Transplantation," *Transplantation Proceedings* 24(6):2546, Appleton & Lange, United States (1992).

Yang, Y-F., et al., "Enhanced Induction of Antitumor T-Cell Responses by Cytotoxic T Lymphocyte-associated Molecule-4 Blockade: The Effect Is Manifested Only at the Restricted Tumor-bearing Stages," *Cancer Research* 57:4036-4041, American Association for Cancer Research, United States (1997).

Japan Platform for Patent Information, unverified English language machine translation of JP 2008-297315 A, published Dec. 11, 2008.

Meng, F., et al., "Acquired Resistance to Chemotherapy in Human Cholangiocarcinoma Is Mediated by an Interleukin (il-6) Dependent Activation of the X-Linked Inhibitor of Apoptosis (xiap) Protein," *Gastroenterology* 128(4):Supplemental 2:A-30, Abstract No. 165 (2005).

Meng, F., et al., "Over-expression of interleukin-6 enhances cell survival and transformed cell growth in human malignant cholangiocytes," *Journal of Hepatology* 44:1055-1065, Elsevier B.V., Netherlands (2006).

Ozaki, H., et al., "Effectiveness of Multimodality Treatment for Resectable Pancreatic Cancer," *International Journal of Pancreatology* 7:195-200, Humana Press, United States (1990).

Skurkovich, S.V., et al., "Anticytokine therapy—new approach to the treatment of autoimmune and cytokine-disturbance diseases," *Med. Hypotheses* 59(6):770-780, Eden Press, United States (2002) (Russian).

Office Action mailed Sep. 26, 2011, in U.S. Appl. No. 12/094,644, Nakashima, J., et al., filed Nov. 24, 2006, U.S. Patent and Trademark Office, Alexandria, VA.

Office Action mailed Aug. 16, 2011, in U.S. Appl. No. 12/161,733, Ishida, S., filed Jan. 26, 2007, U.S. Patent and Trademark Office, Alexandria, VA.

Patel et al. (2005) J. Pharmacol. Exp. Ther. 312(3): 1170-1178, American Society for Pharmacology and Experimental Therapeutics.

Skurkovich et al. (2002) Med. Hypothesis 59(6): 770-780, (English revelant portion).

Y. Ohsugi and N. Tsuchimoto, Pharmacological and Clinical Profile of Humanized Anti-human IL-6 Receptor Anibody (Tocilizumab), a Therapeutic Drug for Castleman's Disease, *Folia Pharmacol. Jpn.* 126:419-425, Japan (2005).

Unverified English language translation of Y. Ohsugi and N. Tsuchimoto, Pharmacological and Clinical Profile of Humanized Anti-Human IL-6 Receptor Anibody (Tocilizumab), a Therapeutic Drug for Castleman's Disease, *Folia Pharmacol. Jpn.* 126:419-425, Japan (2005).

Rudikoff, S., et al., "Single amino acid substitution altering antigen-binding specificity," *Proc. Natl. Acad. Sci. USA* 79:1979-1983, United States (1982).

Akari, M., et al., "Efficacy of the Anti-IL-6 Receptor Antibody Tocilizumab in Neuromyelitis Optica," *Neurology* 82:1302-1306, American Academy of Neurology, United States (2014).

Barkhof, F., et al., "Comparison of MRI Criteria at First Presentation to Predict Conversion to Clinically Definite Multiple Sclerosis," *Brain* 120:2059-2069, Oxford University Press, United Kingdom (1997).

Chihara, N., et al., "Interleukin 6 Signaling Promotes Anti-Aquaporin 4 Autoantibody Production from Plasmablasts in Neuromyelitis Optica," *Proc. Nat. Acad. Sci.* 108(9):3701-3706, United States (2011).

Chihara et al., "Autoantibody Producing Cells in Neuromyelitis Optica," *Journal of Clinical and Experimental Medicine* 240:534-535 (2012).

Christensen, J.R., et al., "Systemic Inflammation in Progressive Multiple Sclerosis Involves Follicular T-Helper, TH17- and Activated B-Cells and Correlates with Progression," *PLos ONE* 8(3):e57820 (2013).

Hosokawa et al., "The Response to Treatment with Interferon beta-1 b in Patients with Multiple Sclerosis," *Shinkei Chiryo* 25(5):589-595 (2008).

Houzen, H., et al., "Increased Prevalence, Incidence, and Female Predominance of Multiple Sclerosis in Northern Japan," *J. Neural. Sci.* 323:117-122, Elsevier B.V., Netherlands (2012).

Kakuron III, "Section 9 Opticospinal Multiple Sclerosis," *Tahatsusei Kokasho Chiryo Guideline* 2010:104-109 (2010).

Lucchinetti, C., et al., "Heterogeneity of Multiple Sclerosis Lesions: Implications for the Pathogenesis of Demyelination," *Ann. Neural.* 47:707-717, American Neurological Association, United States (2000).

Miller, D.H., et al., "Differential Diagnosis of Suspected Multiple Sclerosis: A Consensus Approach," *Multiple Sclerosis* 14:1157-1174, SAGE Publications, United States (2008).

Nakamura, M., et al., "IL-6-dependent Plasmablasts in Pathological Conditions of Relapsing-Remitting Multiple Sclerosis," *Jpn. J. Clin. Immunol.* 36:345, W5-5, Japan Society for Clinical Immunology, Japan (2013).

Nakamura, M., et al., "Clinical Features of Multiple Sclerosis with High Plasmablast Frequency in Peripheral Blood," Poster Session of 54th Annual Meeting of the Japanese Society of Neurology in Tokyo, Japan (presented Jun. 1, 2013).

Nakamura, M., et al., "Clinical Characteristics of Multiple Sclerosis with High Peripheral Blood Plasmablast Frequency," a meeting abstract of 54th Annual Meeting of the Japanese Society of Neurology in Tokyo, Japan (published Apr. 30, 2013).

Nakamura, M., et al., "Clinical Features of Multiple Sclerosis with High Plasmablast Frequency in Peripheral Blood," Poster Session, Multiple Sclerosis, Keystone Symposia on Molecular and Cellular Biology, Big Sky, Montana, United States (presented Jan. 14, 2013).

Nakamura, M., et al., "Clinical Features of Multiple Sclerosis with High Plasmablast Frequency in Peripheral Blood," Abstract, Multiple Sclerosis, Keystone Symposia on Molecular and Cellular Biology, Big Sky, Montana, United States (published online Dec. 11, 2012).

Nakamura, M., et al., "Clinical Features of Multiple Sclerosis with High Plasmablast Frequency in Peripheral Blood," Abstract for Poster Session, Multiple Sclerosis, Keystone Symposia on Molecular and Cellular Biology, Big Sky, Montana, United States (distributed Jan. 11, 2013).

Nakamura, M., et al., "Plasmablast in the Pathology of Multiple Sclerosis," *Jpn. J. Clin. Immounol.* 38(5):403-411, The Japan Society for Clinical Immunology, Japan (2015).

Shimizu, J., et al., "IFNβ-1b May Severely Exacerbate Japanese Optic-Spinal MS in Neuromyelitis Optica Spectrum," *Neurology* 75:1423-1427, AAN Enterprises, United States (2010).

Srivastava, R., et al., "Potassium Channel KIR4.1 as an Immune Target in Multiple Sclerosis," *N. Engl. J. Med.* 367:115-123 United States (2012).

Tintoré, M., et al., "Isolated Demyelinating Syndromes: Comparison of Different MR Imaging Criteria to Predict Conversion to

(56) References Cited

OTHER PUBLICATIONS

Clinically Definite Multiple Sclerosis," *AJNR Am. J. Neuroradiol.* 21:702-706, American Society of Neuroradiology, United States (2000).

Waubant, E., et al., "Clinical Characteristics of Responders to Interferon Therapy for Relapsing MS," *Neurology* 61:184-189, AAN Enterprises, United States (2003).

* cited by examiner

CHRONIC REJECTION INHIBITOR

TECHNICAL FIELD

The present invention relates to agents for suppressing chronic rejection reaction, which comprise an IL-6 inhibitor as an active ingredient, and uses thereof. The present invention also relates to methods for suppressing chronic rejection reaction, which comprise the step of administering an IL-6 inhibitor to recipients.

BACKGROUND ART

IL-6 is a cytokine also called B-cell stimulating factor 2 (BSF2) or interferon β2. IL-6 was discovered as a differentiation factor involved in the activation of B-cell lymphocytes (Non-Patent Document 1), and was later revealed to be a multifunctional cytokine that influences the function of various cells (Non-Patent Document 2). IL-6 has been reported to induce maturation of T lymphocyte cells (Non-Patent Document 3).

IL-6 transmits its biological activity via two kinds of proteins on cells. The first is the IL-6 receptor, which is a ligand binding protein to which IL-6 binds, with a molecular weight of about 80 kDa (Non-Patent Documents 4 and 5). The IL-6 receptor is present in a membrane-bound form that penetrates and is expressed on the cell membrane, and also as a soluble IL-6 receptor that mainly consists of the extracellular region of the membrane-bound form.

The other kind of protein is the membrane protein gp130, which has a molecular weight of about 130 kDa and is involved in non-ligand binding signal transduction. The biological activity of IL-6 is transmitted into the cell through formation of an IL-6/IL-6 receptor complex by IL-6 and IL-6 receptor, followed by binding of the complex with gp130 (Non-Patent Document 6).

IL-6 inhibitors are substances that inhibit the transmission of IL-6 biological activity. Currently, known IL-6 inhibitors include antibodies against IL-6 (anti-IL-6 antibodies), antibodies against IL-6 receptor (anti-IL-6 receptor antibodies), antibodies against gp130 (anti-gp130 antibodies), IL-6 variants, partial peptides of IL-6 or IL-6 receptor, and such.

There are several reports regarding anti-IL-6 receptor antibodies (Non-Patent Documents 7 and 8, and Patent Documents 1 to 3). One such report details a humanized PM-1 antibody, which is obtained by transplanting the complementarity determining region (CDR) of mouse antibody PM-1 (Non-Patent Document 9), which is an anti-IL-6 receptor antibody, into a human antibody (Patent Document 4).

Due to advances in multidrug therapy and clinical application of various immunosuppressants, therapeutic strategies for the acute rejection reaction that follow organ transplantation are almost established, and the one-year survival rate after various organ transplantations has been significantly improved. However, the chronic rejection reaction, which becomes problematic from after a year following transplantation, occurs even in clinical cases where the acute rejection reaction has been overcome by conventional immunosuppressive therapy, and where that therapy has been continued for a long term. Thus, neither preventive nor therapeutic methods effective against the chronic rejection reaction have been established. Furthermore, the mechanism behind this pathological condition has not been fully elucidated, and it is difficult to diagnose it compared to the acute rejection reaction. Thus, the chronic rejection reaction is known to be a complication that affects long-term prognosis in recipients (Non-Patent Documents 10 and 11).

Known pathological features characteristic of the chronic rejection reaction include fibrosis of interstitium and stenosis of lumens due to intimal thickening of luminal tissues in transplanted organs. In particular, angiostenosis is an important pathological feature, and is referred to as post-transplantation vascular lesion or post-transplantation arteriosclerosis. A variety of factors is thought to intricately influence the progression of the pathological condition, such as prolongation of the rejection reaction by both cellular and humoral immunity, ischemia-reperfusion disorders of organs, functional disorders of vascular endothelia, common risk factors for arteriosclerosis (diabetes, hyperlipidemia, hypertension, and the like) in recipients, side effects of immunosuppressants, genetic factors, and post-transplantation infection of cytomegalovirus (Non-Patent Documents 12 and 13).

Among existing pharmaceutical agents, calcineurin inhibitors such as cyclosporine and tacrolimus in particular are ineffective towards the chronic rejection reaction, and their side effects such as hypertension, hyperlipidemia, and diabetes are considered problematic. Further, long-term immunosuppressive therapy after transplantation is required in pediatric recipients in particular. Thus, the development of pharmaceutical agents effective for the chronic rejection reaction and having few side effects (Non-Patent Documents 13 and 14) has been anticipated.

The above-described requirement to develop a novel immunosuppressive therapy for suppressing the chronic rejection reaction is the background of the present study.

Documents of related prior arts for the present invention are described below.

[Patent Document 1] International Patent Application Publication No. WO 95/09873
[Patent Document 2] French Patent Application No. FR 2694767
[Patent Document 3] U.S. Pat. No. 5,216,128
[Patent Document 4] WO 92/19759
[Non-Patent Document 1] Hirano, T. et al., Nature (1986) 324, 73-76
[Non-Patent Document 2] Akira, S. et al., Adv. in Immunology (1993) 54, 1-78
[Non-Patent Document 3] Lotz, M. et al., J. Exp. Med. (1988) 167, 1253-1258
[Non-Patent Document 4] Taga, T. et al., J. Exp. Med. (1987) 166, 967-981
[Non-Patent Document 5] Yamasaki, K. et al., Science (1988) 241, 825-828
[Non-Patent Document 6] Taga, T. et al., Cell (1989) 58, 573-581
[Non-Patent Document 7] Novick, D. et al., Hybridoma (1991) 10, 137-146
[Non-Patent Document 8] Huang, Y. W. et al., Hybridoma (1993) 12, 621-630
[Non-Patent Document 9] Hirata, Y. et al., J. Immunol. (1989) 143, 2900-2906
[Non-Patent Document 10] Wong, B. W. et al., Cardiovasc. Pathol. (2005) 14, 176-80
[Non-Patent Document 11] Hornick, P. et al., Methods Mol. Biol. (2006) 333, 131-44
[Non-Patent Document 12] Ramzy, D. et al., Can. J. Surg. (2005) 48, 319-327
[Non-Patent Document 13] Valantine, H., J. Heart Lung Transplant (2004) 23(5 Suppl), S187-93
[Non-Patent Document 14] Webber, S. A. et al., Lancet (2006) 368, 53-69

[Non-Patent Document 15] Izawa, A., et al., Circ. J. (2007) 71(Suppl I), 392 (Annual Scientific Meeting of the Japanese Circulation Society, Kobe, Mar. 15-Mar. 17, 2007; Abstract PE-269)

[Non-Patent Document 16] Izawa, A., et al., Am. J. Transplant. (2007) 7(Suppl 11), 426 (American Transplant Congress, San Francisco, Calif., Mar. 5-Mar. 9, 2007; Abstract 1084)

DISCLOSURE OF THE INVENTION

Problems to be Solved by the Invention

The present invention was conducted under the circumstances described above. An objective of the present invention is to provide agents for suppressing the chronic rejection reaction, which comprise an IL-6 inhibitor as active ingredients. A further objective of the present invention is to provide methods for suppressing the chronic rejection reaction, which comprise the step of administering an IL-6 inhibitor to subjects.

Means for Solving the Problems

To achieve the objectives described above, the present inventors tested anti-IL-6 receptor antibodies for the effect of suppressing the chronic rejection reaction.

The present inventors assessed the chronic rejection reaction-suppressing effect of anti-mouse IL-6 receptor antibody (MR16-1) administration using a mouse model for post-heart-transplantation chronic rejection. The result of histopathological analysis of the transplanted hearts extirpated 60 days after transplantation revealed that fibrosis of myocardium and vascular stenotic lesions, which are pathological conditions characteristic of the chronic rejection reaction, were significantly suppressed in the MR16-1-treated group as compared to the control group. Thus, MR16-1 administration was demonstrated to have the effect of suppressing the chronic rejection reaction.

Thus, the present inventors discovered for the first time that administering anti-IL-6 receptor antibodies suppresses the rejection reaction in the chronic phase after organ transplantation, and thus completed the present invention.

More specifically, the present invention provides the following inventions:

[1] an agent for suppressing chronic rejection reaction, comprising as an active ingredient an IL-6 inhibitor;

[2] the agent for suppressing chronic rejection reaction of [1], wherein the IL-6 inhibitor is an antibody that recognizes an IL-6;

[3] the agent for suppressing chronic rejection reaction of [1], wherein the IL-6 inhibitor is an antibody that recognizes an IL-6 receptor;

[4] the agent for suppressing chronic rejection reaction of [2] or [3], wherein the antibody is a monoclonal antibody;

[5] the agent for suppressing chronic rejection reaction of [2] or [3], wherein the antibody is an antibody that recognizes a human IL-6 or human IL-6 receptor;

[6] the agent for suppressing chronic rejection reaction of [2] or [3], wherein the antibody is a recombinant antibody;

[7] the agent for suppressing chronic rejection reaction of any one of [2] to [6], wherein the antibody is a chimeric, humanized, or human antibody;

[8] the agent for suppressing chronic rejection reaction of any one of [1] to [7], which is used to suppress chronic rejection reaction in heart transplantation;

[9] a method for suppressing chronic rejection reaction, which comprises the step of administering an IL-6 inhibitor to a subject;

[10] the method of [9], wherein the IL-6 inhibitor is an antibody that recognizes an IL-6;

[11] the method of [9], wherein the IL-6 inhibitor is an antibody that recognizes an IL-6 receptor;

[12] the method of [10] or [11], wherein the antibody is a monoclonal antibody;

[13] the method of [10] or [11], wherein the antibody is an antibody that recognizes a human IL-6 or human IL-6 receptor;

[14] the method of [10] or [11], wherein the antibody is a recombinant antibody;

[15] the method of any one of [10] to [14], wherein the antibody is a chimeric, humanized, or human antibody;

[16] the method of any one of [9] to [15], which suppresses chronic rejection reaction in heart transplantation;

[17] use of an IL-6 inhibitor in producing an agent for suppressing chronic rejection reaction;

[18] the use of [17], wherein the IL-6 inhibitor is an antibody that recognizes an IL-6;

[19] the use of [17], wherein the IL-6 inhibitor is an antibody that recognizes an IL-6 receptor;

[20] the use of [18] or [19], wherein the antibody is a monoclonal antibody;

[21] the use of [18] or [19], wherein the antibody is an antibody that recognizes a human IL-6 or human IL-6 receptor;

[22] the use of [18] or [19], wherein the antibody is a recombinant antibody;

[23] the use of any one of [18] to [22], wherein the antibody is a chimeric, humanized, or human antibody; and

[24] an IL-6 inhibitor for use in suppressing chronic rejection reaction.

MODE FOR CARRYING OUT THE INVENTION

The present inventors discovered that administration of an anti-IL-6 receptor antibody can suppress the chronic rejection reaction. The present invention is based on these findings.

The present invention relates to agents for suppressing the chronic rejection reaction, which comprise an IL-6 inhibitor as an active ingredient.

Herein, an "IL-6 inhibitor" is a substance that blocks IL-6-mediated signal transduction and inhibits IL-6 biological activity. Preferably, the IL-6 inhibitor is a substance that has an inhibitory function against the binding of IL-6, IL-6 receptor, or gp130.

The IL-6 inhibitors of the present invention include, but are not limited to, for example, anti-IL-6 antibodies, anti-IL-6 receptor antibodies, anti-gp130 antibodies, IL-6 variants, soluble IL-6 receptor variants, and partial peptides of IL-6 or IL-6 receptor, and low molecular weight compounds and proteins (for example, C326 Avimer (Nature Biotechnology (2005) 23, 1556-61)) that show similar activities. Preferable IL-6 inhibitors of the present invention include antibodies that recognize IL-6 receptors.

The source of the antibodies is not particularly restricted in the present invention; however, the antibodies are preferably derived from mammals, and more preferably derived from humans.

The anti-IL-6 antibodies used in the present invention can be obtained as polyclonal or monoclonal antibodies using known means. In particular, monoclonal antibodies derived from mammals are preferred as the anti-IL-6 antibodies used in the present invention. Monoclonal antibodies derived from mammals include those produced from hybridomas and those produced by genetic engineering methods from hosts transformed with an expression vector that comprises an antibody gene. By binding to IL-6, the antibody inhibits IL-6 from binding to an IL-6 receptor and thus blocks the transmission of IL-6 biological activity into the cell.

Such antibodies include, MH166 (Matsuda, T. et al., But J. Immunol. (1988) 18, 951-956), SK2 antibody (Sato, K. et al., transaction of the 21$^{st}$ Annual Meeting of the Japanese Society for Immunology (1991) 21, 166), and so on.

Basically, anti-IL-6 antibody-producing hybridomas can be prepared using known techniques, as follows: Specifically, such hybridomas can be prepared by using IL-6 as a sensitizing antigen to carry out immunization using a conventional immunization method, fusing the obtained immune cells with known parent cells by a conventional cell fusion method, and screening for monoclonal antibody-producing cells using a conventional screening method.

More specifically, anti-IL-6 antibodies can be produced as follows: For example, human IL-6 for use as the sensitizing antigen for obtaining antibodies can be obtained using the IL-6 gene and/or amino acid sequences disclosed in Eur. J. Biochem. (1987) 168, 543-550; J. Immunol. (1988) 140, 1534-1541; and/or Agr. Biol. Chem. (1990) 54, 2685-2688.

After transforming an appropriate host cell with a known expression vector system inserted with an IL-6 gene sequence, the desired IL-6 protein is purified using known methods from the inside of the host cell or from the culture supernatant. This purified IL-6 protein may be used as a sensitizing antigen. Alternatively, a fusion protein of the IL-6 protein and another protein may be used as a sensitizing antigen.

Anti-IL6 receptor antibodies used for the present invention can be obtained as polyclonal or monoclonal antibodies by using known methods. In particular, the anti-IL-6 receptor antibodies used in the present invention are preferably monoclonal antibodies derived from mammals. The monoclonal antibodies derived from mammals include those produced from hybridomas and those produced using genetic engineering methods from hosts transformed with an expression vector that comprises an antibody gene. By binding to an IL-6 receptor, the antibodies inhibit IL-6 from binding to the IL-6 receptor, and thus block the transmission of IL-6 biological activity into the cell.

Such antibodies include, MR16-1 antibody (Tamura, T. et al., Proc. Natl. Acad. Sci. USA (1993) 90, 11924-11928); PM-1 antibody (Hirata, Y et al., J. Immunol. (1989) 143, 2900-2906); AUK12-20 antibody, AUK64-7 antibody and AUK146-15 antibody (International Patent Application Publication No. WO 92/19759), and so on. Of these, the PM-1 antibody can be exemplified as a preferred monoclonal antibody against the human IL-6 receptor, and the MR16-1 antibody as a preferred monoclonal antibody against the mouse IL-6 receptor.

Basically, hybridomas producing an anti-IL-6 receptor monoclonal antibody can be prepared using known techniques, as follows: Specifically, such hybridomas can be prepared by using an IL-6 receptor as the sensitizing antigen to carry out immunization by a conventional immunization method, fusing the obtained immune cells with a known parent cell using a conventional cell fusion method, and screening for monoclonal antibody-producing cells using a conventional screening method.

More specifically, anti-IL-6 receptor antibodies can be produced as follows: For example, a human IL-6 receptor or mouse IL-6 receptor for use as a sensitizing antigen for obtaining antibodies can be obtained by using the IL-6 receptor genes and/or amino acid sequences disclosed in European Patent Application Publication No. EP 325474 and Japanese Patent Application Kokai Publication No. (JP-A) 1103-155795 (unexamined, published Japanese patent application), respectively.

There are two kinds of IL-6 receptor proteins: one expressed on the cell membrane and the other detached from the cell membrane (soluble IL-6 receptors) (Yasukawa, K. et al., J. Biochem. (1990) 108, 673-676). The soluble IL-6 receptor consists essentially of the extracellular region of the cell membrane-bound IL-6 receptor, and differs from the membrane-bound IL-6 receptor in that it lacks the transmembrane region or both the transmembrane and intracellular regions. Any IL-6 receptor may be employed as an IL-6 receptor protein, so long as it can be used as a sensitizing antigen for producing an anti-IL-6 receptor antibody used in the present invention.

After transforming an appropriate host cell with a known expression vector system inserted with an IL-6 receptor gene sequence, the desired IL-6 receptor protein is purified from the inside of the host cell or from the culture supernatant using a known method. This purified IL-6 receptor protein may be used as a sensitizing antigen. Alternatively, a cell expressing the IL-6 receptor or a fusion protein of the IL-6 receptor protein and another protein may be used as a sensitizing antigen.

Anti-gp130 antibodies used in the present invention can be obtained as polyclonal or monoclonal antibodies by using known methods. In particular, the anti-gp130 antibodies used in the present invention are preferably monoclonal antibodies derived from mammals. Mammal-derived monoclonal antibodies include those produced from hybridomas and those produced using genetic engineering methods from hosts transformed with an expression vector that comprises an antibody gene. By binding to gp130, the antibody inhibits gp130 from binding to the IL-6/IL-6 receptor complex, and thus blocks transmission of IL-6 biological activity into the cell.

Such antibodies include, AM64 antibody (JP-A (Kokai) H03-219894), 4B11 antibody and 2H4 antibody (U.S. Pat. No. 5,571,513), B-S12 antibody and B-P8 antibody (JP-A (Kokai) H08-291199), and so on.

Basically, anti-gp130 monoclonal antibody-producing hybridomas can be prepared using known techniques, as follows: Specifically, such hybridomas can be prepared by using gp130 as a sensitizing antigen to carry out the immunization using a conventional immunization method, fusing the obtained immune cells with a known parent cell by a conventional cell fusion method, and screening for monoclonal antibody-producing cells using a conventional screening method.

More specifically, monoclonal antibodies can be produced as follows: For example, gp130 for use as a sensitizing antigen for obtaining antibodies can be obtained using the gp130 gene and/or amino acid sequence disclosed in European Patent Application Publication No. EP 411946.

After transforming an appropriate host cell with a known expression vector system inserted with a gp130 gene sequence, the desired gp130 protein is purified by a known method from the inside of the host cell or from the culture supernatant. This purified gp130 protein may be used as a sensitizing antigen. Alternatively, a cell expressing gp130 or a fusion protein of the gp130 protein and another protein may be used as a sensitizing antigen.

Mammals to be immunized with a sensitizing antigen are not particularly limited, but are preferably selected considering compatibility with the parent cell used for cell fusion. Generally, rodents such as mice, rats, and hamsters are used.

Animals are immunized with sensitizing antigens according to known methods. For example, as a general method, animals are immunized by intraperitoneal or subcutaneous injection of a sensitizing antigen. Specifically, the sensitizing antigen is preferably diluted or suspended in an appropriate amount of phosphate-buffered saline (PBS), physiological saline or such, mixed with an appropriate amount of a general adjuvant (e.g., Freund's complete adjuvant), emulsified, and then administered to a mammal several times, every four to 21 days. In addition, an appropriate carrier may be used for immunization with a sensitizing antigen.

Following such immunization, an increased level of a desired antibody in serum is confirmed and then immune cells are obtained from the mammal for cell fusion. Preferred immune cells for cell fusion include, in particular, spleen cells.

The mammalian myeloma cells used as parent cells, i.e. as partner cells to be fused with the above immune cells, include various known cell strains, for example, P3X63Ag8.653 (Kearney, J. F. et al., J. Immunol (1979) 123, 1548-1550), P3X63Ag8U.1 (Current Topics in Microbiology and Immunology (1978) 81, 1-7), NS-1 (Kohler, G. and Milstein, C., Eur. J. Immunol. (1976) 6, 511-519), MPC-11 (Margulies, D. H. et al., Cell (1976) 8, 405-415), SP2/0 (Shulman, M. et al., Nature (1978) 276, 269-270), F0 (de St. Groth, S. F. et al., J. Immunol. Methods (1980) 35, 1-21), S194 (Trowbridge, I. S., J. Exp. Med. (1978) 148, 313-323), R210 (Galfre, C. et al., Nature (1979) 277, 131-133), and such.

Basically, cell fusion of the aforementioned immune cells and myeloma cells can be performed using known methods, for example, the method of Milstein et al. (Kohler, G and Milstein, C., Methods Enzymol. (1981) 73, 3-46), and such.

More specifically, the aforementioned cell fusion is achieved in general nutrient culture medium in the presence of a cell fusion enhancing agent. For example, polyethylene glycol (PEG), Sendai virus (HVJ), and such are used as fusion enhancing agents. Further, to enhance fusion efficiency, auxiliary agents such as dimethyl sulfoxide may be added depending on needs.

The ratio of immune cells to myeloma cells used is preferably, for example, 1 to 10 immune cells for each myeloma cell. The culture medium used for the aforementioned cell fusion is, for example, the RPMI1640 or MEM culture medium, which are suitable for proliferation of the aforementioned myeloma cells. A general culture medium used for culturing this type of cell can also be used. Furthermore, serum supplements such as fetal calf serum (FCS) can be used in combination.

For cell fusion, the fusion cells (hybridomas) of interest are formed by mixing predetermined amounts of an aforementioned immune cell and myeloma cell in an aforementioned culture medium, and then adding and mixing a concentration of 30% to 60% (w/v) PEG solution (e.g., a PEG solution with a mean molecular weight of about 1,000 to 6,000) pre-heated to about 37° C. Then, cell fusion agents and such that are unsuitable for the growth of hybridomas can be removed by repeatedly adding an appropriate culture medium and then removing the supernatant by centrifugation.

The above hybridomas are selected by culturing cells in a general selection culture medium, for example, HAT culture medium (a culture medium containing hypoxanthine, aminopterin, and thymidine). Culture in HAT culture medium is continued for a sufficient period, generally several days to several weeks, to kill cells other than the hybridomas of interest (unfused cells). Then, a standard limited dilution method is performed to screen and clone hybridomas that produce an antibody of interest.

In addition to the methods for immunizing non-human animals with antigens for obtaining the aforementioned hybridomas, desired human antibodies with the activity of binding to a desired antigen or antigen-expressing cell can be obtained by sensitizing a human lymphocyte with a desired antigen protein or antigen-expressing cell in vitro, and fusing the sensitized B lymphocyte with a human myeloma cell (e.g., U266) (see, Japanese Patent Application Kokoku Publication No. (JP-B) H01-59878 (examined, approved Japanese patent application published for opposition)). Further, a desired human antibody can be obtained by administering an antigen or antigen-expressing cell to a transgenic animal that has a repertoire of human antibody genes, and then following the aforementioned method (see International Patent Application Publication Nos. WO 93/12227, WO 92/03918, WO 94/02602, WO 94/25585, WO 96/34096, and WO 96/33735).

The thus-prepared hybridomas which produce monoclonal antibodies can be subcultured in a conventional culture medium and stored in liquid nitrogen for a long period.

When obtaining monoclonal antibodies from the aforementioned hybridomas, the following methods may be employed: (1) methods where the hybridomas are cultured according to conventional methods and the antibodies are obtained as a culture supernatant; (2) methods where the hybridomas are proliferated by administering them to a compatible mammal and the antibodies are obtained as ascites; and so on. The former method is preferred for obtaining antibodies with high purity, and the latter is preferred for large-scale antibody production.

For example, anti-IL-6 receptor antibody-producing hybridomas can be prepared by the method disclosed in JP-A (Kokai) H03-139293. Such hybridomas can be prepared by injecting a PM-1 antibody-producing hybridoma into the abdominal cavity of a BALB/c mouse, obtaining ascites, and then purifying a PM-1 antibody from the ascites; or by culturing the hybridoma in an appropriate medium (e.g., RPM:11640 medium containing 10% fetal bovine serum, and 5% BM-Condimed H1 (Boehringer Mannheim); hybridoma SFM medium (GIBCO-BRL); PFHM-II medium (GIBCO-BRL), etc.) and then obtaining PM-1 antibody from the culture supernatant.

Recombinant antibodies can be used as the monoclonal antibodies of the present invention, wherein the antibodies are produced using genetic recombination techniques by cloning an antibody gene from a hybridoma, inserting the gene into an appropriate vector, and then introducing the vector into a host (see, for example, Borrebaeck, C. A. K. and Larrick, J. W., Therapeutic Monoclonal Antibodies, published in the United Kingdom by Macmillan Publishers Ltd, 1990).

More specifically, mRNAs coding for antibody variable (V) regions are isolated from cells that produce antibodies of interest, such as hybridomas. mRNAs can be isolated by preparing total RNAs according to known methods, such as the guanidine ultracentrifugation method (Chirgwin, J. M. et al., Biochemistry (1979) 18, 5294-5299) and the AGPC method (Chomczynski, P. et al., Anal. Biochem. (1987) 162, 156-159), and preparing mRNAs using the mRNA Purification Kit (Pharmacia) and such. Alternatively, mRNAs can be directly prepared using a QuickPrep mRNA Purification Kit (Pharmacia).

cDNAs of the antibody V regions are synthesized from the obtained mRNAs using reverse transcriptase. cDNAs may be synthesized using an AMV Reverse Transcriptase First-strand cDNA Synthesis Kit and so on. Further, to synthesize and amplify the cDNAs, the 5'-RACE method (Frohman, M. A. et al., Proc. Natl. Acad. Sci. USA (1988) 85, 8998-9002; Belyaysky, A. et al., Nucleic Acids Res. (1989) 17, 2919-2932) using 5'-Ampli FINDER RACE Kit (Clontech) and PCR may be employed. A DNA fragment of interest is purified from the obtained PCR products and then ligated with a vector DNA. Then, a recombinant vector is prepared using the above DNA and introduced into *Escherichia coli* (*E. coli*) or such, and then its colonies are selected to prepare a desired recombinant vector. The nucleotide sequence of the DNA of interest is confirmed by, for example, the dideoxy method.

When a DNA encoding the V region of an antibody of interest is obtained, the DNA is ligated with a DNA that encodes a desired antibody constant region (C region), and inserted into an expression vector. Alternatively, a DNA encoding an antibody V region may be inserted into an expression vector comprising a DNA of an antibody C region.

To produce an antibody to be used in the present invention, as described below, an antibody gene is inserted into an expression vector such that it is expressed under the control of an expression regulating region, for example, an enhancer and promoter. Then, the antibody can be expressed by transforming a host cell with this expression vector.

In the present invention, to reduce heteroantigenicity against humans and such, artificially modified genetic recombinant antibodies, for example, chimeric antibodies, humanized antibodies, or human antibodies, can be used. These modified antibodies can be prepared using known methods.

A chimeric antibody can be obtained by ligating a DNA encoding an antibody V region, obtained as above, with a DNA encoding a human antibody C region, then inserting the DNA into an expression vector and introducing it into a host for production (see, European Patent Application Publication No. EP 125023; International Patent Application Publication No. WO 92/19759). This known method can be used to obtain chimeric antibodies useful for the present invention.

Humanized antibodies are also referred to as reshaped human antibodies, and are antibodies wherein the complementarity determining regions (CDRs) of an antibody from a mammal other than human (e.g., a mouse antibody) are transferred into the CDRs of human antibodies. General methods for this gene recombination are also known (see, European Patent Application Publication No. EP 125023, International Patent Application Publication No. WO 92/19759).

More specifically, DNA sequences designed such that the CDRs of a mouse antibody are ligated with the framework regions (FRs) of a human antibody are synthesized by PCR from several oligonucleotides produced to contain overlapping portions at their termini. The obtained DNA is ligated with a human antibody C region-encoding DNA and then inserted into an expression vector. The expression vector is introduced into a host to produce the humanized antibody (see, European Patent Application Publication No. EP 239400, International Patent Application Publication No. WO 92/19759).

The human antibody FRs to be ligated via the CDRs are selected so that the CDRs form suitable antigen binding sites. The amino acid(s) within the FRs of the antibody variable regions may be substituted as necessary so that the CDRs of the reshaped human antibody form an appropriate antigen binding site (Sato, K. et al., Cancer Res. (1993) 53, 851-856). Human antibody C regions are used for the chimeric and humanized antibodies, and include Cγ. For example, Cγ1, Cγ2, Cγ3, or Cγ4 may be used. Furthermore, to improve the stability of the antibodies or their production, the human antibody C regions may be modified.

Chimeric antibodies consist of the variable region of an antibody derived from a non-human mammal and the constant region of an antibody derived from a human; humanized antibodies consist of the CDRs of an antibody derived from a non-human mammal and the framework regions and constant regions derived from a human antibody. Both have reduced antigenicity in the human body, and are thus useful as antibodies for use in the present invention.

Preferred specific examples of humanized antibodies for use in the present invention include the humanized PM-1 antibody (see, International Patent Application Publication No. WO 92/19759).

Furthermore, in addition to the aforementioned methods for obtaining human antibodies, techniques for obtaining human antibodies by panning using a human antibody library are also known. For example, the variable regions of human antibodies can be expressed on phage surfaces as single chain antibodies (scFv) by using the phage display method, and antigen-binding phages can then be selected. By analyzing the genes of the selected phages, DNA sequences coding for the human antibody variable regions that bind to the antigen can be determined. Once the DNA sequence of an scFv that binds to the antigen is revealed, an appropriate expression vector comprising the sequence can be constructed to obtain a human antibody. These methods are already known, and the publications of WO 92/01047, WO 92/20791, WO93/06213, WO 93/11236, WO 93/19172, WO 95/01438, and WO 95/15388 can be used as reference.

The antibody genes constructed above can be expressed according to conventional methods. When a mammalian cell is used, the antibody gene can be expressed using a DNA in which the antibody gene to be expressed is functionally ligated to a useful commonly used promoter and a poly A signal downstream of the antibody gene, or a vector comprising the DNA. Examples of a promoter/enhancer include the human cytomegalovirus immediate early promoter/enhancer.

Furthermore, other promoters/enhancers that can be used for expressing the antibodies for use in the present invention include viral promoters/enhancers from retroviruses, polyoma viruses, adenoviruses, simian virus 40 (SV40), and such; and also include mammalian cell-derived promoters/enhancers such as human elongation factor 1α (HEF1α).

For example, when the SV40 promoter/enhancer is used, the expression can be easily performed by following the method by Mulligan et al. (Mulligan, R. C. et al., Nature (1979) 277, 108-114). Alternatively, in the case of the HEF1α promoter/enhancer, the method by Mizushima et al. (Mizushima, S. and Nagata S., Nucleic Acids Res. (1990) 18, 5322) can be used.

When *E. coli* is used, an antibody gene can be expressed by functionally ligating a conventional promoter, a signal sequence for antibody secretion, and the antibody gene to be expressed. Examples of the promoter include a lacZ promoter, araB promoter and such. When a lacZ promoter is used, genes can be expressed according to the method of Ward et al. (Ward, E. S. et al., Nature (1989) 341, 544-546; Ward, E. S. et al., FASEB J. (1992) 6, 2422-2427); and the araB promoter may be used according to the method of Better et al. (Better, M. et al., Science (1988) 240, 1041-1043).

When the antibody is produced into the periplasm of E. coli, the pel B signal sequence (Lei, S. P. et al., J. Bacteriol. (1987) 169, 4379-4383) may be used as a signal sequence for antibody secretion. The antibodies produced into the periplasm are isolated, and then used after appropriately refolding the antibody structure (see, for example, WO 96/30394).

As the replication origin, those derived from SV40, polyoma virus, adenovirus, bovine papilloma virus (BPV) and such may be used. In addition, to enhance the gene copy number in a host cell system, the expression vector may comprise the aminoglycoside phosphotransferase (APH) gene, thymidine kinase (TK) gene, E. coli xanthine-guanine phosphoribosyltransferase (Ecogpt) gene, dihydrofolate reductase (dhfr) gene, or such as a selection marker.

Any production system may be used to prepare the antibodies for use in the present invention. The production systems for antibody preparation include in vitro and in vivo production systems. In vitro production systems include those using eukaryotic cells or prokaryotic cells.

Production systems using eukaryotic cells include those using animal cells, plant cells, or fungal cells. Such animal cells include (1) Mammalian cells, for example, CHO, COS, myeloma, baby hamster kidney (BHK), HeLa, Vero, and such; (2) amphibian cells, for example, Xenopus oocyte; and (3) insect cells, for example, sf9, sf21, Tn5, and such. Known plant cells include cells derived from Nicotiana tabacum, which may be cultured as a callus. Known fungal cells include yeasts such as Saccharomyces (e.g., S. cerevisiae), mold fungi such as Aspergillus (e.g., A. niger), and such.

Production systems using prokaryotic cells include those using bacterial cells. Known bacterial cells include E. coli and Bacillus subtilis.

Antibodies can be obtained by using transformation to introduce an antibody gene of interest into these cells, and then culturing the transformed cells in vitro. Cultures are conducted according to known methods. For example, DMEM, MEM, RPMI1640, IMDM may be used as the culture medium, and serum supplements such as FCS may be used in combination. Further, cells introduced with antibody genes may be transferred into the abdominal cavity or such of an animal to produce the antibodies in vivo.

On the other hand, in vivo production systems include those using animals or plants. Production systems using animals include those that use mammals or insects.

Mammals that can be used include goats, pigs, sheep, mice, bovines and such (Vicki Glaser, SPECTRUM Biotechnology Applications, 1993). Further, insects that can be used include silkworms. When using plants, tobacco may be used, for example.

An antibody gene is introduced into these animals or plants, the antibody is produced in the body of the animals or plants, and this antibody is then recovered. For example, an antibody gene can be prepared as a fusion gene by inserting it into the middle of a gene encoding a protein such as goat β casein, which is uniquely produced into milk. DNA fragments comprising the fusion gene, which includes the antibody gene, are injected into goat embryos, and the embryos are introduced into female goats. The desired antibody is obtained from milk produced by the transgenic animals born to the goats that received the embryos, or produced from progenies of these animals. The transgenic goats can be given hormones to increase the volume of milk containing the desired antibody that they produce (Ebert, K. M. et al., Bio/Technology (1994) 12, 699-702).

When silkworms are used, the silkworms are infected with a baculovirus inserted with a desired antibody gene, and the desired antibody is obtained from the body fluids of these silkworms (Maeda, S. et al., Nature (1985) 315, 592-594). Moreover, when tobacco is used, the desired antibody gene is inserted into a plant expression vector (e.g., pMON530) and the vector is introduced into bacteria such as Agrobacterium tumefaciens. This bacterium is used to infect tobacco (e.g., Nicotiana tabacum) such that desired antibodies can be obtained from the leaves of this tobacco (Julian, K.-C. Ma et al., Eur. J. Immunol. (1994) 24, 131-138).

When producing antibodies using in vitro or in vivo production systems, as described above, DNAs encoding an antibody heavy chain (H chain) and light chain (L chain) may be inserted into separate expression vectors and a host is then co-transformed with the vectors. Alternatively, the DNAs may be inserted into a single expression vector for transforming a host (see International Patent Application Publication No. WO 94/11523).

The antibodies used in the present invention may be antibody fragments or modified products thereof, so long as they can be suitably used in the present invention. For example, antibody fragments include Fab, F(ab')2, Fv, and single chain Fv (scFv), in which the Fvs of the H and L chains are linked via an appropriate linker.

Specifically, the antibody fragments are produced by treating antibodies with enzymes, for example, papain or pepsin, or alternatively, genes encoding these fragments are constructed, introduced into expression vectors, and these are expressed in appropriate host cells (see, for example, Co, M. S. et al., J. Immunol. (1994) 152, 2968-2976; Better, M. & Horwitz, A. H., Methods in Enzymology (1989) 178, 476-496; Plueckthun, A. & Skerra, A., Methods in Enzymology (1989) 178, 497-515; Lamoyi, E., Methods in Enzymology (1989) 121, 652-663; Rousseaux, J. et al., Methods in Enzymology (1989) 121, 663-666; Bird, R. E. et al., TIBTECH (1991) 9, 132-137).

An scFv can be obtained by linking the H-chain V region and the L-chain V region of an antibody. In the scFv, the H-chain V region and the L-chain V region are linked via a linker, preferably via a peptide linker (Huston, J. S. et al., Proc. Natl. Acad. Sci. USA (1988) 85, 5879-5883). The V regions of the H and L chains in an scFv may be derived from any of the antibodies described above. Peptide linkers for linking the V regions include, for example, arbitrary single chain peptides consisting of 12 to 19 amino acid residues.

An scFv-encoding DNA can be obtained by using a DNA encoding an H chain or a V region and a DNA encoding an L chain or a V region of the aforementioned antibodies as templates, using PCR to amplify a DNA portion that encodes the desired amino acid sequence in the template sequence and uses primers that define the termini of the portion, and then further amplifying the amplified DNA portion with a DNA that encodes a peptide linker portion and primer pairs that link both ends of the linker to the H chain and L chain.

Once an scFv-encoding DNA has been obtained, an expression vector comprising the DNA and a host transformed with the vector can be obtained according to conventional methods. In addition, scFv can be obtained according to conventional methods using the host.

As above, these antibody fragments can be produced from the host by obtaining and expressing their genes. Herein, an "antibody" encompasses such antibody fragments.

Antibodies bound to various molecules, such as polyethylene glycol (PEG), may also be used as modified antibodies. Herein, an "antibody" encompasses such modified antibodies. These modified antibodies can be obtained by chemically modifying the obtained antibodies. Such methods are already established in the art.

Antibodies produced and expressed as above can be isolated from the inside or outside of the cells or from the hosts, and then purified to homogeneity. The antibodies for use in the present invention can be isolated and/or purified using affinity chromatography. Columns to be used for the affinity chromatography include, for example, protein A columns and protein G columns. Carriers used for the protein A columns include, for example, HyperD, POROS, Sepharose FF and such. In addition to the above, other methods used for the isolation and/or purification of common proteins may be used, and are not limited in any way.

For example, the antibodies used for the present invention may be isolated and/or purified by appropriately selecting and combining chromatographies in addition to affinity chromatography, filters, ultrafiltration, salting-out, dialysis, and such. Chromatographies include, for example, ion-exchange chromatography, hydrophobic chromatography, gel filtration, and such. These chromatographies can be applied to high performance liquid chromatography (HPLC). Alternatively, reverse phase HPLC may be used.

The concentration of the antibodies obtained as above can be determined by absorbance measurement, ELISA, or such. Specifically, absorbance is determined by appropriately diluting the antibody solution with PBS(−), measuring absorbance at 280 nm, and calculating the concentration (1.35 OD=1 mg,/ml). Alternatively, when using ELISA, the measurement can be performed as follows: Specifically, 100 µl of goat anti-human IgG (TAG) diluted to 1 µg/ml with 0.1 M bicarbonate buffer (pH 9.6) is added to a 96-well plate (Nunc) and incubated overnight at 4° C. to immobilize the antibody. After blocking, 100 µl of an appropriately diluted antibody of the present invention or an appropriately diluted sample comprising the antibody, and human IgG (CAPPEL) are added as a standard, and incubated for one hour at room temperature.

After washing, 100 µl of 5,000× diluted alkaline phosphatase-labeled anti-human IgG (BIO SOURCE) is added and incubated for one hour at room temperature. After another wash, substrate solution is added and incubated, and the absorbance at 405 nm is measured using a Microplate Reader Model 3550 (Bio-Rad) to calculate the concentration of the antibody of interest.

The IL-6 variants used in the present invention are substances with the activity of binding to an IL-6 receptor and which do not transmit IL-6 biological activity. That is, the IL-6 variants compete with IL-6 to bind to IL-6 receptors, but fail to transmit IL-6 biological activity, and hence they block IL-6-mediated signal transduction.

The IL-6 variants are produced by introducing mutation(s) by substituting amino acid residues in the amino acid sequence of IL-6. The origin of IL-6 used as the base of the IL-6 variants is not limited, but is preferably human IL-6 in consideration of antigenicity and such.

More specifically, amino acid substitutions are performed by predicting the secondary structure of the IL-6 amino acid sequence using known molecular modeling programs (e.g., WHATIF; Vriend et al., J. Mol. Graphics (1990) 8, 52-56), and further assessing the influence of the substituted amino acid residue(s) on the whole molecule. After determining the appropriate amino acid residue to be substituted, commonly performed PCR methods are carried out using a nucleotide sequence encoding a human IL-6 gene as a template, and mutations are introduced to cause amino acids substitutions, and thus genes encoding IL-6 variants are obtained. If needed, this gene is inserted into an appropriate expression vector, and the IL-6 variant can be obtained by applying the aforementioned methods for expression, production, and purification of recombinant antibodies.

Specific examples of the IL-6 variants are disclosed in Brakenhoff et al., J. Biol. Chem. (1994) 269, 86-93, Savino et al., EMBO J. (1994) 13, 1357-1367, WO 96/18648, and WO 96/17869.

The partial peptides of IL-6 and of the IL-6 receptor to be used in the present invention are substances with the activity of binding to the IL-6 receptor and to IL-6, respectively, and which do not transmit IL-6 biological activity. Namely, by binding to and capturing an IL-6 receptor or IL-6, the IL-6 partial peptides or IL-6 receptor partial peptides can specifically inhibit IL-6 from binding to the IL-6 receptor. As a result, the biological activity of IL-6 is not transmitted, and IL-6-mediated signal transduction is blocked.

The partial peptides of IL-6 or IL-6 receptor are peptides that comprise part or all of the amino acid sequence of the region of the IL-6 or IL-6 receptor amino acid sequence that is involved in the binding between the IL-6 and IL-6 receptor. Such peptides usually comprise ten to 80, preferably 20 to 50, more preferably 20 to 40 amino acid residues.

The IL-6 partial peptides or IL-6 receptor partial peptides can be produced according to generally known methods, for example, genetic engineering techniques or peptide synthesis methods, by specifying the region of the IL-6 or IL-6 receptor amino acid sequence that is involved in the binding between the IL-6 and IL-6 receptor, and using a portion or entirety of the amino acid sequence of the specified region.

When preparing an IL-6 partial peptide or IL-6 receptor partial peptide using genetic engineering methods, a DNA sequence encoding the desired peptide is inserted into an expression vector, and then the peptide can be obtained by applying the aforementioned methods for expressing, producing, and purifying recombinant antibodies.

When producing an IL-6 partial peptide or IL-6 receptor partial peptide by using peptide synthesis methods, generally used peptide synthesis methods, for example, solid phase synthesis methods or liquid phase synthesis methods, may be used.

Specifically, the peptides can be synthesized according to the method described in "Continuation of Development of Pharmaceuticals, Vol. 14, Peptide Synthesis (in Japanese) (ed. Haruaki Yajima, 1991, Hirokawa Shoten)". As a solid phase synthesis method, for example, the following method can be employed: the amino acid corresponding to the C terminus of the peptide to be synthesized is bound to a support that is insoluble in organic solvents, then the peptide strand is elongated by alternately repeating (1) the reaction of condensing amino acids, whose α-amino groups and branch chain functional groups are protected with appropriate protecting groups, one at a time in a C- to N-terminal direction; and (2) the reaction of removing the protecting groups from the a-amino groups of the resin-bound amino acids or peptides. Solid phase peptide synthesis is broadly classified into the Boc method and the Fmoc method, depending on the type of protecting groups used.

After synthesizing a protein of interest as above, deprotection reactions are carried out, then the peptide strand is cleaved from its support. For the peptide strand cleavage reaction, hydrogen fluoride or trifluoromethane sulfonic acid is generally used for the Boc method, and TFA is generally used for the Fmoc method. In the Boc method, for example, the above-mentioned protected peptide resin is treated with hydrogen fluoride in the presence of anisole. Then, the peptide is recovered by removing the protecting groups and cleaving the peptide from its support. By freeze-drying the recovered peptide, a crude peptide can be obtained. In the Fmoc method, on the other hand, the deprotection reaction and the reaction to cleave the peptide strand from the support can be performed in TFA using a method similar to those described above, for example.

Obtained crude peptides can be separated and/or purified by applying HPLC. Elution may be performed under optimum conditions using a water-acetonitrile solvent system, which is generally used for protein purification. The fractions corresponding to the peaks of the obtained chromatographic profile are collected and freeze-dried. Thus, purified peptide fractions are identified by molecular weight analysis via mass spectrum analysis, amino acid composition analysis, amino acid sequence analysis, or such.

Specific examples of IL-6 partial peptides and IL-6 receptor partial peptides are disclosed in JP-A (Kokai) H02-188600, JP-A (Kokai) H07-324097, JP-A (Kokai) H08-311098, and United States Patent Publication No. U.S. Pat. No. 5,210,075.

The antibodies used in the present invention may also be conjugated antibodies that are bound to various molecules, such as polyethylene glycol (PEG), radioactive substances, and toxins. Such conjugated antibodies can be obtained by chemically modifying the obtained antibodies. Methods for modifying antibodies are already established in the art. The "antibodies" of the present invention encompass these conjugated antibodies.

The agents of the present invention for suppressing chronic rejection reaction, which comprise IL-6 inhibitors as active ingredients, can be used to treat chronic rejection reaction. The present invention also provides agents for suppressing chronic rejection reaction in heart transplantation, which comprise an IL-6 inhibitor as active ingredient.

A rejection reaction that is suppressed by the suppressing agents of the present invention is preferably the chronic rejection reaction, which is a problem in actual transplantation medicine. The chronic rejection reaction is a complication characterized by the intimal thickening of blood vessels and fibrosis of interstitium, which becomes problematic from after one year post-transplantation and affects the long-term prognosis of recipients. The chronic rejection reaction gradually progresses even after the acute rejection reaction is clinically overcome.

The present inventors have previously discovered the therapeutic effect of IL-6 inhibitors in a mouse model for post-heart-transplantation acute rejection (WO2007/058194). The mechanism for pathological conditions of the acute rejection reaction mainly mediated by cytotoxic T cells is assumed to be different from that of the chronic rejection reaction. Specific evidences suggesting that the chronic rejection reaction is different from the acute rejection reaction are as follows:

(1) the chronic rejection reaction is a specific pathological condition with cell growth, such as fibrosis of interstitium and stenosis lesion due to the intimal thickening in luminal tissues of transplanted organs;
(2) the onset of the chronic rejection reaction cannot be suppressed by conventional immunosuppressive therapy that is effective in suppressing the acute rejection reaction;
(3) the chronic rejection reaction is an immunological response that latently progresses even after the acute rejection is clinically overcome; and
(4) the chronic rejection reaction has risk factors characteristic of its onset.

(1) Vascular stenotic lesions accompanied by the growth of vascular smooth muscle cells caused by vascular endothelial injury is known to be a histopathological feature characteristic of the chronic rejection reaction. Such vascular stenotic lesions are also referred to as post-transplantation vascular lesions or post-transplantation arteriosclerosis. These results in circulatory disorders due to impaired blood flow in transplanted organs, and the transplanted organs cease to function. Thus, vascular stenotic lesions have become problematic as a serious complication at the chronic stage. Causes of vascular injuries in transplanted organs include ischemia-reperfusion disorders, oxidative stress, and the acute rejection reaction at transplantation surgery. Thus, some successful results have indeed been achieved in suppressing the chronic rejection reaction because of the advancement of techniques for suppressing the acute rejection reaction and maintaining organs in the acute phase. However, no definitive preventive methods have been available. In addition, (2) there is no established immunosuppressive therapy effective for the chronic rejection reaction. (3) Latently-progressing rejection reaction includes prolongation of humoral immunity mediated by isoantibodies and prolongation of a variety of cellular immunity mediated by infiltration of macrophages and various cytokines. (4) A variety of risk factors are known to be involved in the chronic rejection reaction, including side effects of immunosuppressants, genetic factors, post-transplantation infection (cytomegalovirus and such), and deposition of antibodies in tissues as well as common risk factors for arteriosclerosis (diabetes, hyperlipidemia, hypertension) in recipients. Thus, dysfunction of transplanted organs is assumed to occur due to complicated participation of various factors.

In the present invention, "suppression of chronic rejection reaction after transplantation" refers to suppression of the above-described various symptoms associated with the chronic rejection reaction, such as fibrosis of interstitium and stenosis due to intimal thickening of luminal tissues in transplanted organs.

The types of organ transplantations for which the suppressing agents of the present invention can be used are not particularly limited, and preferred organs for the organ transplantations in the present invention include parenchymal organs, such as hearts, livers, kidneys, pancreas, lungs, and small intestines. The present invention can also be applied to transplantation of tissues such as cardiac valves, vessels, skin, bones, and corneas.

In the present invention, the activity of IL-6 inhibitors in inhibiting the transduction of IL-6 signals can be evaluated by conventional methods. Specifically, IL-6 is added to cultures of IL-6-dependent human myeloma cell lines (S6B45 and KPMM2), human Lennert T lymphoma cell line KT3, or IL-6-dependent cell line MH60.BSF2; and the $^3$H-thymidine uptake by the IL-6-dependent cells is measured in the presence of an IL-6 inhibitor. Alternatively, IL-6 receptor-expressing U266 cells are cultured, and $^{125}$I-labeled IL-6 and an IL-6 inhibitor are added to the culture at the same time; and then $^{125}$I-labeled IL-6 bound to the IL-6 receptor-expressing cells is quantified. In addition to the IL-6 inhibitor group, a negative control group that does not contain an IL-6 inhibitor is included in the assay system described above. The activity of the IL-6 inhibitor to inhibit IL-6 can be evaluated by comparing the results of both groups.

Furthermore, whether a post-transplantation rejection reaction is suppressed can be assessed as follows: in organ transplantation, the "suppression of post-transplant injury" can also be assumed to be achieved when the graft survival is improved as a result. Graft survival can be assessed based on whether each organ functions normally after transplantation.

As described in the Examples below, the chronic rejection reaction in heart transplantation was demonstrated to be suppressed by administering an anti-IL-6 receptor antibody. This suggests that IL-6 inhibitors such as anti-IL-6 receptor antibodies are useful as agents for suppressing the chronic rejection reaction.

Subjects to be administered with the suppressing agents of the present invention are mammals. The mammals are preferably humans.

The suppressing agents of the present invention can be administered as pharmaceuticals, and may be administered systemically or locally via oral or parenteral administration. For example, intravenous injections such as drip infusions, intramuscular injections, intraperitoneal injections, subcutaneous injections, suppositories, enemas, oral enteric tablets, or the like can be selected. Appropriate administration methods can be selected depending on a patient's age and symptoms. The effective dose per administration is selected from the range of 0.01 to 100 mg/kg body weight. Alternatively, the dose may be selected from the range of 1 to 1000 mg/patient, preferably from the range of 5 to 50 mg/patient. A preferred dose and administration method are as follows: For example, when an anti-IL-6 receptor antibody is used, the effective dose is an amount such that free antibody is present in the blood. Specifically, a dose of 0.5 to 40 mg/kg body weight/month (four weeks), preferably 1 to 20 mg/kg body weight/month is administered via an intravenous injection such as a drip infusion, subcutaneous injection or such, once to several times a month, for example, twice a week, once a week, once every two weeks, or once every four weeks. The administration schedule may be adjusted by, for example, extending the administration interval of twice a week or once a week to once every two weeks, once every three weeks, or once every four weeks, while monitoring the condition after transplantation and changes in the blood test values.

In the present invention, the suppressing agents may contain pharmaceutically acceptable carriers, such as preservatives and stabilizers. "Pharmaceutically acceptable carriers" refer to materials that can be co-administered with an above-described agent; and may or may not themselves produce the above-described effect of suppressing chronic rejection reaction. Alternatively, the carriers may be materials that do not have the effect of suppressing chronic rejection reaction, but that produce an additional or synergistic stabilizing effect when used in combination with an IL-6 inhibitor.

Such pharmaceutically acceptable materials include, for example, sterile water, physiological saline, stabilizers, excipients, buffers, preservatives, surfactants, chelating agents (EDTA and such), and binders.

In the present invention, surfactants include non-ionic surfactants, and typical examples of such include sorbitan fatty acid esters such as sorbitan monocaprylate, sorbitan monolaurate, and sorbitan monopalmitate; glycerin fatty acid esters such as glycerin monocaprylate, glycerin monomyristate and glycerin monostearate; polyglycerin fatty acid esters such as decaglyceryl monostearate, decaglyceryl distearate, and decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, and polyoxyethylene sorbitan tristearate; polyoxyethylene sorbit fatty acid esters such as polyoxyethylene sorbit tetrastearate and polyoxyethylene sorbit tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol, polyoxyethylene polyoxypropylene propyl ether, and polyoxyethylene polyoxypropylene cetyl ether; polyoxyethylene alkyl phenyl ethers such as polyoxyethylene nonylphenyl ether; polyoxyethylene hardened castor oils such as polyoxyethylene castor oil and polyoxyethylene hardened castor oil (polyoxyethylene hydrogenated castor oil); polyoxyethylene beeswax derivatives such as polyoxyethylene sorbit beeswax; polyoxyethylene lanolin derivatives such as polyoxyethylene lanolin; and polyoxyethylene fatty acid amides and such with an HLB of six to 18, such as polyoxyethylene stearic acid amide.

Surfactants also include anionic surfactants, and typical examples of such include, for example, alkylsulfates having an alkyl group with ten to 18 carbon atoms, such as sodium cetylsulfate, sodium laurylsulfate, and sodium oleylsulfate; polyoxyethylene alkyl ether sulfates in which the alkyl group has ten to 18 carbon atoms and the average molar number of added ethylene oxide is 2 to 4, such as sodium polyoxyethylene lauryl sulfate; alkyl sulfosuccinate ester salts having an alkyl group with eight to 18 carbon atoms, such as sodium lauryl sulfosuccinate ester; natural surfactants, for example, lecithin; glycerophospholipids; sphingophospholipids such as sphingomyelin; and sucrose fatty acid esters in which the fatty acids have 12 to 18 carbon atoms.

One, two or more of the surfactants described above can be combined and added to the agents of the present invention. Surfactants that are preferably used in the preparations of the present invention include polyoxyethylene sorbitan fatty acid esters, such as polysorbates 20, 40, 60, and 80. Polysorbates 20 and 80 are particularly preferred. Polyoxyethylene polyoxypropylene glycols, such as poloxamer (Pluronic F-68® and such), are also preferred.

The amount of surfactant added varies depending on the type of surfactant used. When polysorbate 20 or 80 is used, the amount is in general in the range of 0.001 to 100 mg/ml, preferably in the range of 0.003 to 50 mg/ml, more preferably in the range of 0.005 to 2 mg/ml.

In the present invention, buffers include phosphate, citrate buffer, acetic acid, malic acid, tartaric acid, succinic acid, lactic acid, potassium phosphate, gluconic acid, capric acid, deoxycholic acid, salicylic acid, triethanolamine, fumaric acid, and other organic acids; and carbonic acid buffer, Tris buffer, histidine buffer, and imidazole buffer.

Liquid preparations may be formulated by dissolving the agents in aqueous buffers known in the liquid preparation field. The buffer concentration is in general in the range of 1 to 500 mM, preferably in the range of 5 to 100 mM, more preferably in the range of 10 to 20 mM.

The agents of the present invention may also comprise other low-molecular-weight polypeptides; proteins such as serum albumin, gelatin, and immunoglobulin; amino acids; sugars and carbohydrates such as polysaccharides and monosaccharides, sugar alcohols, and such.

Herein, amino acids include basic amino acids, for example, arginine, lysine, histidine, and ornithine, and inorganic salts of these amino acids (preferably hydrochloride salts, and phosphate salts, namely phosphate amino acids). When free amino acids are used, the pH is adjusted to a preferred value by adding appropriate physiologically acceptable buffering substances, for example, inorganic acids, and in particular hydrochloric acid, phosphoric acid, sulfuric acid, acetic acid, and formic acid, and salts thereof. In this case, the use of phosphate is particularly beneficial because it gives quite stable freeze-dried products. Phosphate is particularly advantageous when preparations do not substantially contain organic acids, such as malic acid, tartaric acid, citric acid, succinic acid, and fumaric acid, or do not contain corresponding anions (malate ion, tartrate ion, citrate ion, succinate ion, fumarate ion, and such). Preferred amino acids are arginine, lysine, histidine, and ornithine. Acidic amino acids can also be used, for example, glutamic acid and aspartic acid, and salts thereof (preferably sodium salts); neutral amino acids, for example, isoleucine, leucine, glycine, serine, threonine, valine, methionine, cysteine, and alanine; and aromatic amino acids, for example, phenylalanine, tyrosine, tryptophan, and its derivative, N-acetyl tryptophan.

Herein, sugars and carbohydrates such as polysaccharides and monosaccharides include, for example, dextran, glucose, fructose, lactose, xylose, mannose, maltose, sucrose, trehalose, and raffinose.

Herein, sugar alcohols include, for example, mannitol, sorbitol, and inositol.

When the agents of the present invention are prepared as aqueous solutions for injection, the agents may be mixed with, for example, physiological saline, and/or isotonic solution containing glucose or other auxiliary agents (such as D-sorbitol, D-mannose, D-mannitol, and sodium chloride). The aqueous solutions may be used in combination with appropriate solubilizing agents such as alcohols (ethanol and such), polyalcohols (propylene glycol, PEG, and such), or non-ionic surfactants (polysorbate 80 and HCO-50).

The agents may further comprise, if required, diluents, solubilizers, pH adjusters, soothing agents, sulfur-containing reducing agents, antioxidants, and such.

Herein, the sulfur-containing reducing agents include, for example, compounds comprising sulfhydryl groups, such as N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and thioalkanoic acids having one to seven carbon atoms.

Moreover, the antioxidants in the present invention include, for example, erythorbic acid, dibutylhydroxy toluene, butylhydroxy anisole, a-tocopherol, tocopherol acetate, L-ascorbic acid and salts thereof, L-ascorbic acid palmitate, L-ascorbic acid stearate, sodium hydrogen sulfite, sodium sulfite, triamyl gallate, propyl gallate, and chelating agents such as disodium ethylenediamine tetraacetate (EDTA), sodium pyrophosphate, and sodium metaphosphate.

If required, the agents may be encapsulated in microcapsules (microcapsules of hydroxymethylcellulose, gelatin, poly[methylmethacrylic acid] or such) or prepared as colloidal drug delivery systems (liposome, albumin microspheres, microemulsion, nano-particles, nano-capsules, and such) (see "Remington's Pharmaceutical Science 16$^{th}$ edition", Oslo Ed., 1980, and the like). Furthermore, methods for preparing agents as sustained-release agents are also known, and are applicable to the present invention (Langer et al., J. Biomed. Mater. Res. (1981) 15, 167-277; Langer, Chem. Tech. (1982) 12, 98-105; U.S. Pat. No. 3,773,919; European Patent Application No. (EP) 58,481; Sidman et al., Biopolymers (1983) 22, 547-556; and EP 133,988).

Pharmaceutically acceptable carriers used are appropriately selected from those described above or combined depending on the type of dosage form, but are not limited thereto.

The present invention relates to methods for suppressing the chronic rejection reaction, which comprise the step of administering IL-6 inhibitors to subjects.

The present invention also relates to methods for suppressing the chronic rejection reaction in heart transplantation, which comprise the step of administering IL-6 inhibitors to subjects.

Herein, the "subject" refers to the organisms or organism body parts to be administered with an IL-6 inhibitor of the present invention. The organisms include animals (for example, human, domestic animal species, and wild animals) but are not particularly limited. The "organism body parts" are not particularly limited.

Herein, "administration" includes oral and parenteral administration. Oral administration includes, for example, administration of oral agents. Such oral agents include, for example, granules, powders, tablets, capsules, solutions, emulsions, and suspensions.

Parenteral administration includes, for example, administration of injections. Such injections include, for example, intravenous injections, subcutaneous injections, intramuscular injections, and intraperitoneal injection. Meanwhile, the effects of the methods of the present invention can be achieved by introducing genes comprising oligonucleotides to be administered to living bodies using gene therapy techniques. Alternatively, the agents of the present invention may be administered locally to intended areas of treatment. For example, the agents can be administered by local injection during surgery, use of catheters, or targeted gene delivery of DNAs encoding peptides of the present invention.

The suppressing agents of the present invention may be administered to subjects prior to organ transplantation, at the time of organ transplantation, or after organ transplantation. Further, the suppressing agents may be administered once or repeatedly.

Alternatively, when administered to an excised or delivered part of an organism, the suppressing agents of the present invention may be "contacted" with the organism part.

In the present invention, "contacting" is performed according to the condition of the organism. Examples include spraying the suppressing agents of the present invention over the organism parts, and adding the suppressing agents of the present invention to crushed organism parts, but are not limited thereto. When the organism part is cultured cells, the above-mentioned "contact" can be achieved by adding the suppressing agents of the present invention to culture medium of these cells, or by introducing DNAs comprising oligonucleotides of the present invention into cells that constitute the organism part.

When conducting the methods of the present invention, the agents of the present invention may be administered as parts of pharmaceutical compositions in combination with at least one known chemotherapeutant. Alternatively, the agents of the present invention may be administered simultaneously with at least one known immunosuppressant. In one embodiment, the known chemotherapeutants and the suppressing agents of the present invention may be administered virtually simultaneously.

The agents for suppressing the chronic rejection reaction of the present invention is preferably administered systemically, but may be administered to sites of organ transplantation after the organ have been transplanted, or may be administered to targets at the same time as the organ. Alternatively, the agents may be added to the organ ex vivo, prior to transplantation.

Any patents, published patent applications, and publications cited herein are incorporated by reference.

EXAMPLES

Figure 1:
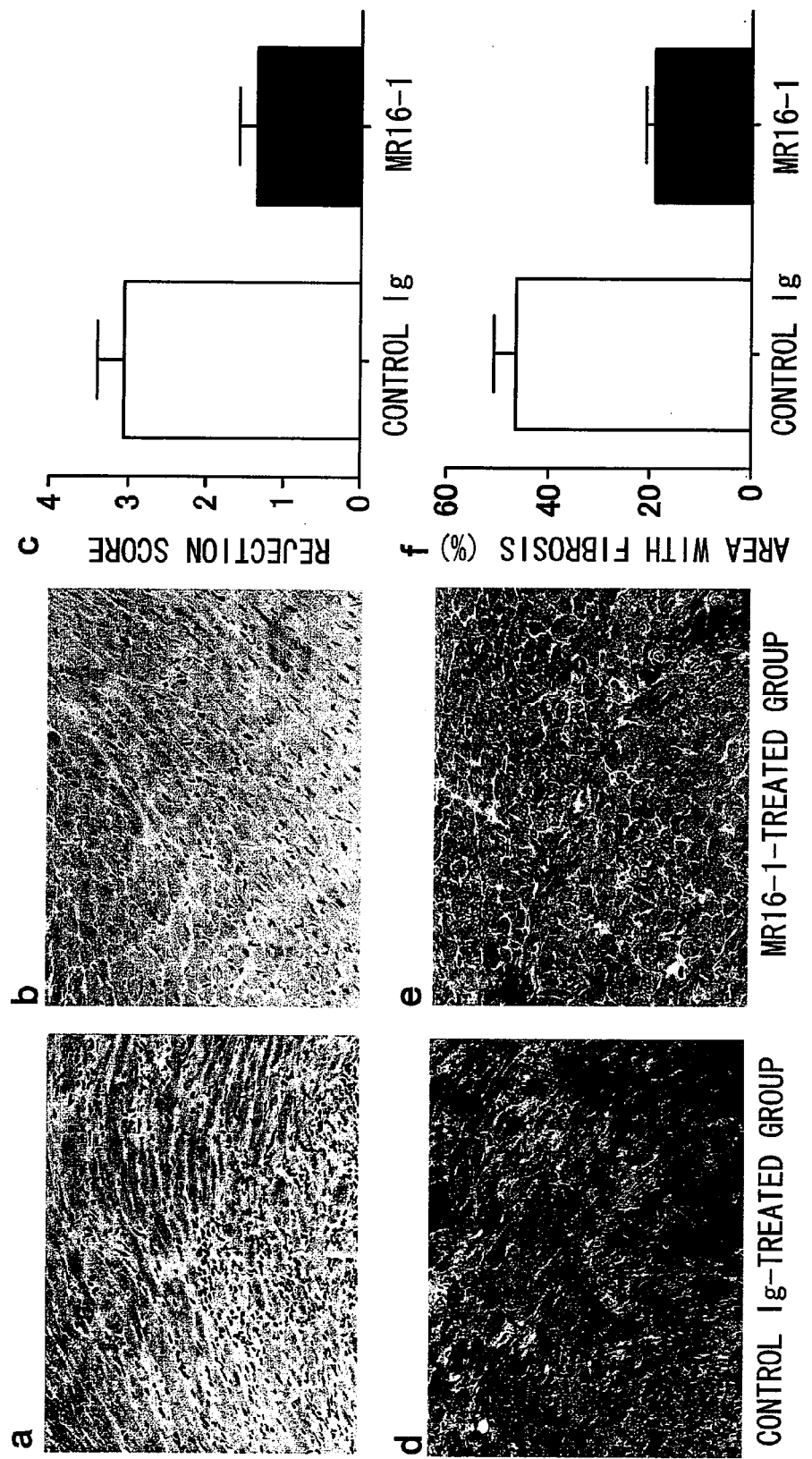
FIG. 1 shows graphs and photographs depicting the result of a comparison and assessment based on rejection scores in histopathological sections of the transplanted hearts 60 days after transplantation and the ratio of area with fibrosis.

Hereinbelow, the present invention will be specifically described with reference to Examples, but it is not to be construed as being limited thereto.

As donors, B6.C-H2$^{bm12}$ mice were purchased via Charles River Laboratories Japan Inc. from Jackson Laboratory (Bar Harbor, Me.) in the United States. As recipients, C57BL/6 mice were purchased from Japan SLC, Inc. There are only minor MHC antigen mismatches (class II mismatching) between the two mouse strains so that the acute rejection reaction to transplanted hearts does not occur, while the histopathological features observed about two months after transplantation are consistent with those of the human chronic rejection reaction. Thus, they are established as an animal model for the chronic rejection reaction. The mice were bred in the institute for animal experiments of Shinshu University (formal name: Division of Laboratory Animal Research, Department of Life Science, Research Center for Human and Environmental Sciences, Shinshu University) according to the institution's animal experiment protocols. Mouse heart transplantation was performed using a partially-modified mouse model originating from the previously-reported mouse model for ectopic heart transplantation (Cony, R. J. et al., Transplantation (1973) 16, 343-350). Six- to eight-week-old mice underwent heart transplantation by microsurgery using the procedure described below.

Both donor and recipient mice were anesthetized by intraperitoneally injecting pentobarbital sodium (Nenbutal (trademark)) at a dose of 70 mg/kg. The heart to be transplanted was isolated after ligating vessels other than ascending aorta and pulmonary artery to be used for anastomosis. The isolated heart graft was preserved in cold physiological saline containing 7.5% heparin on ice. The recipient was laparotomized in the midline and the intestines were flipped over to expose the abdominal aorta and inferior vena cava. After blood flow was stopped using microclips for microvessels, an incision of about 1-mm was created on each surface for anastomotic sites. The aorta and the pulmonary artery of the transplanted heart were anastomosed to the abdominal aorta and the inferior vena cava of the recipient, respectively, by continuous suture using 10-0 nylon suture. The microclips were gradually released to resume the blood flow. The transplanted heart was confirmed to resume beating. After confirming hemorrhage arrest, the abdominal wall and the skin were sutured to close the abdomen. Each surgery took about 45 minutes. The success rate was 95% or greater.

In the treatment group, MR16-1 was administered to the peritoneal cavities at a single dose of 0.5 mg/head twice a week. The control treatment group was administered with rat IgG (control Ig) in the same way. Sixty days after transplantation, transplanted hearts were excised from the recipients and chronic rejection reaction was assessed using the following three types of histopathological indicators.

(1) The degree of rejection reaction in the samples stained with hematoxylin-eosin are compared and assessed using rejection scores determined with criteria for five grades from grade 0 to 4 based on the indicators of presence of cell infiltration, and myocardial necrosis and loss (Billingham, M. E. et al., J. Heart Transplant (1990) 9, 587-593; Rodriguez, E. R., J. Heart Lung Transplant (2003) 22, 3-15).

Histopathological sections were prepared from the transplanted hearts 60 days after transplantation, and they were stained with hematoxylin-eosin (FIG. 1). Diffuse infiltration of inflammatory cells and myocardial necrosis were found in the control treatment group (FIG. 1a). In the MR16-1-treated group, infiltration of inflammatory cells was mild and the structure of myocardial tissues remained comparatively intact (FIG. 1b). Furthermore, the rejection score of the MR16-1 administration group was significantly lower than that of the control treatment group (FIG. 1c: control treatment group, 3.1±0.3; MR16-1 administration group, 1.4±0.3; p=0.0013).

(2) Fibrosis of myocardial interstitium characteristic of chronic rejection was detected by Masson's trichrome stain. The ratio (%) of area with fibrosis in each visual field was computed using an image analysis software (NIH image, version 1.62).

The result showed that the area with fibrosis was significantly reduced in the MR16-1-treated group (FIG. 1e) as compared to the control treatment group (FIG. 1d) (FIG. 1f: control treatment group, 46.5%±4.1%; MR16-1 administration group, 19.0%±2.1%; p=0.0001).

(3) To analyze post-transplantation vascular lesions characterized by angiostenosis due to intimal thickening, the percent vascular stenosis was determined by approximately estimating the original vascular lumen from the internal elastic membrane and using the same image analysis software according to the method of Suzuki, J. et al. (Nat. Med. (1997) 3, 900-903) using the following equation:

Percent stenosis (%)=((area of internal elastic membrane)−(lumen))/(area of internal elastic membrane)×100.

Figure 2:
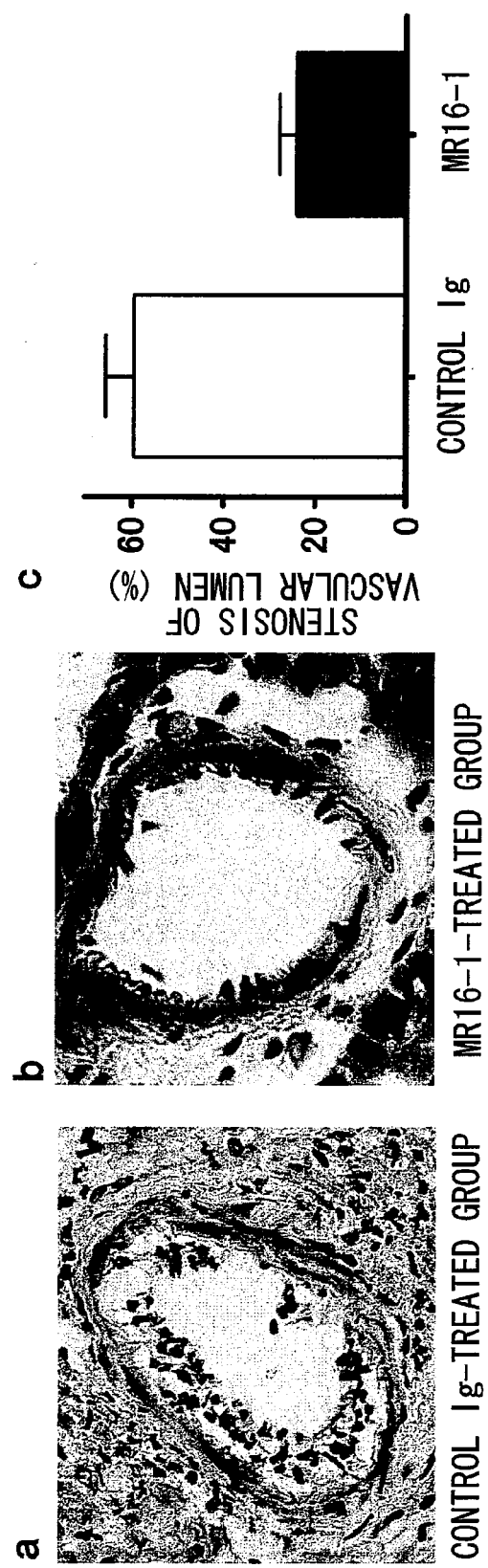
FIG. 2 shows a graph and photographs showing the analysis result for percent vascular stenosis in vascular lesions of the transplanted hearts.

The result obtained by analyzing the vascular lesions in the transplanted hearts showed that the intimal thickening was suppressed and thus the stenosis of vascular lumen was significantly suppressed in the MR16-1-treated group (FIG. 2b) as compared to the control treatment group (FIG. 2a) (FIG. 2c: control treatment group, 59.6%±6.0%; MR16-1 administration group, 23.7%±4.2%; p=0.0019).

As described above, in the mouse heart transplantation model, the administration of MR16-1 to the recipients suppressed chronic rejection reaction to the transplanted hearts and significantly suppressed fibrosis and intimal thickening of blood vessels in the transplanted hearts which are considered to be the characteristic histopathological features. The chronic rejection reaction is a complication that affects long-term prognosis in recipients, and thus novel immunosuppressive therapy is expected to be developed through the clinical application of the agents of the present invention.

INDUSTRIAL APPLICABILITY

The present invention provides agents for suppressing the chronic rejection reaction which comprise an IL-6 inhibitor as an active ingredient, and methods for suppressing the chronic rejection reaction which comprise the step of administering an IL-6 inhibitor to subjects.

The chronic rejection reaction gradually progresses even after the acute-phase rejection reaction is overcome by various immunosuppressants. The pathological condition is complicated and very different in many ways from the acute rejection reaction. The effect of preventing and treating the chronic rejection reaction has not been achieved by any existing pharmaceutical agent. The present invention provides novel therapeutic utilities of IL-6 inhibitors having the effect of suppressing the chronic rejection. Furthermore, since the inhibitors selectively suppress the activity of IL-6, an inflammatory cytokine, they are expected to serve as superior immunosuppressants having fewer side effects as compared to existing pharmaceutical agents.

The invention claimed is:

1. A method for suppressing chronic rejection reaction, which comprises administering a composition comprising an antibody that recognizes an IL-6 receptor to a subject in need thereof prior to organ transplantation, at the time of organ transplantation, or after organ transplantation, thereby suppressing chronic rejection reaction in the subject with a transplanted organ after the organ transplantation, wherein the antibody that recognizes an IL-6 receptor is the only active ingredient in the composition.

2. The method of claim 1, wherein the antibody is a monoclonal antibody.

3. The method of claim 1, wherein the antibody is an antibody that recognizes a human IL-6 receptor.

4. The method of claim 1, wherein the antibody is a recombinant antibody.

5. The method of claim 1, wherein the antibody is a chimeric, humanized, or human antibody.

6. The method of claim 1, which suppresses chronic rejection reaction in heart transplantation.

7. A method of suppressing chronic rejection reaction, which comprises administering an antibody that recognizes an IL-6 receptor to a subject in need thereof prior to organ transplantation, at the time of organ transplantation, or after organ transplantation, thereby suppressing chronic rejection reaction in the subject with a transplanted organ after the organ transplantation, wherein the antibody that recognizes an IL-6 receptor is the only antibody administered.

8. The method of claim 1, wherein the active ingredient suppresses chronic rejection reaction.

* * * * *